United States Patent [19]

Chen et al.

[11] Patent Number: 5,605,796
[45] Date of Patent: Feb. 25, 1997

[54] METHOD FOR PREVENTING AMPLIFICATION OF NUCLEIC ACID CONTAMINANTS IN AMPLIFICATION MIXTURES USING NUCLEASE-RECEPTOR CONJUGATES

[75] Inventors: Yan Chen, Palo Alto; Samuel J. Rose, Los Altos; Edwin F. Ullman, Atherton, all of Calif.

[73] Assignee: Behringwerke AG, Marburg, Germany

[21] Appl. No.: 277,547

[22] Filed: Jul. 19, 1994

[51] Int. Cl.⁶ .............................. C12Q 1/68; C12P 19/34
[52] U.S. Cl. .............. 435/6; 435/91.1; 435/91.2
[58] Field of Search ............................. 435/6, 91.1, 91.2, 435/810

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 4,800,159 | 1/1989 | Mullis et al. | 435/172.3 |
| 4,965,188 | 10/1990 | Mullis et al. | 435/6 |
| 5,008,182 | 4/1991 | Sninsky et al. | 435/5 |
| 5,035,996 | 7/1991 | Hartley | 435/6 |
| 5,116,615 | 5/1992 | Gokcen et al. | 424/94.2 |
| 5,188,963 | 2/1993 | Stapleton | 435/299 |
| 5,273,890 | 12/1993 | Steinman | 435/91.2 |
| 5,427,929 | 6/1995 | Richards et al. | 435/91.2 |

FOREIGN PATENT DOCUMENTS

| | | |
|---|---|---|
| 0381501A2 | 8/1990 | European Pat. Off. . |
| 0439182A2 | 7/1991 | European Pat. Off. . |
| 0473155A2 | 3/1992 | European Pat. Off. . |
| 0496483A2 | 7/1992 | European Pat. Off. . |
| 0522884A1 | 1/1993 | European Pat. Off. . |
| PCT/FR91/00513 | 6/1991 | WIPO . |
| WO91/17270 | 11/1991 | WIPO . |
| WO93/16200 | 8/1993 | WIPO . |

OTHER PUBLICATIONS

Cimino, et al., Nucleic Acids Research, (1991), vol. 19:1 pp. 99–107, "Post–PCR sterilization: a method to control carryover contamination for the polymerase chain reaction".

Corey, et al., Biochemistry, (1989) vol. 28:21 pp. 8277–8286 "Generation of a Catalytic Sequence–Specific Hybrid DNase".

Furrer, et al, Nature, (Jul. 26, 1990) vol. 346: p. 324 "Improving PCR efficiency".

Issacs, et al., Nucleic Acids Research, (1991) vol. 19:1 pp. 109–116, "Post–PCR sterilization: development and application to an HIV–1 diagnostic assay".

Lo, et al., PCR Protocols; A Guide To Methods And Applications, (1990) Academic Press, San Diego, Calif., pp. 113–118 "Incorporation of Biotinylated dUTP".

Longo, et al., Gene, (1990) vol. 93: pp. 125–128, "Use of uracel DNA glycosylase to control carry–over contamination in polymerase chain reactions".

(List continued on next page.)

Primary Examiner—Kenneth R. Horlick
Attorney, Agent, or Firm—Theodore J. Leitereg

[57] ABSTRACT

Methods and kits are disclosed for preventing amplification of contaminating copies of nucleic acids during in amplification of a nucleic acid suspected of being present in a sample. Modified nucleotides that render copies of the nucleic acid bindable by a member of a specific binding pair, such as a receptor, which does not bind to the nucleic acid, are incorporated into copies of the nucleic acid that are produced during the amplification. The sample is combined with an enzyme conjugate, usually a receptor bound to a nuclease, under conditions wherein prior to the amplification the member of a specific binding pair binds to the copies and the enzyme degrades the copies but not the nucleic acid. The methods and kits have particular application to the determination of a nucleic acid analyte.

45 Claims, 3 Drawing Sheets

OTHER PUBLICATIONS

Meier, et al., Journal Of Clinical Microbiology, (Mar. 1993) vol. 31:3 pp. 646–652, "Elimination of Contaminating DNA within Polymerase Chain Reaction Reagents: Implications for a General Approach to Detection of Uncultured Pathogens".

Muralidhar, et al., Gene, (1992) vol. 117 pp. 107–112, "Geometric differences allow differential enzymatic inactivation of PCR product and genomic targets".

Pang, et al., Molecular And Cellular Probes, (1992) vol. 6: pp. 251–256, "Use of modified nucleotides and uracil-DNA glycosylase (UNG) for the control of contamination in the PCR-based amplification of RNA".

Saiki, et al., Science, (Dec. 1985) vol. 230: pp. 1350–1354 "Enzymatic Amplification of β-Globin Genomic Sequences and Restriction Site Analysis for Diagnosis of Sickel Cell Anemia".

Sarkar, et al., Nature, vol. 343: (Jan. 4, 1990) p. 27, "Shedding light on PCR contamination".

Van Brunt, Bio/Technology, vol. 8 (Apr. 1990) pp. 291–294 "Amplifying Genes: PCR and its Alternatives".

Walder, et al., Nucleic Acids Research, (1993) vol. 21:18 pp. 4339–4343, "Use of PCR primers containing a 3'-terminal ribose residue to prevent cross-contamination of amplified sequences".

Zhu, et al., Nucleic Acids Research, (Jan. 28, 1991) vol. 19:9, p. 2511, "The use of exonuclease III for polymerase chain reaction sterilization".

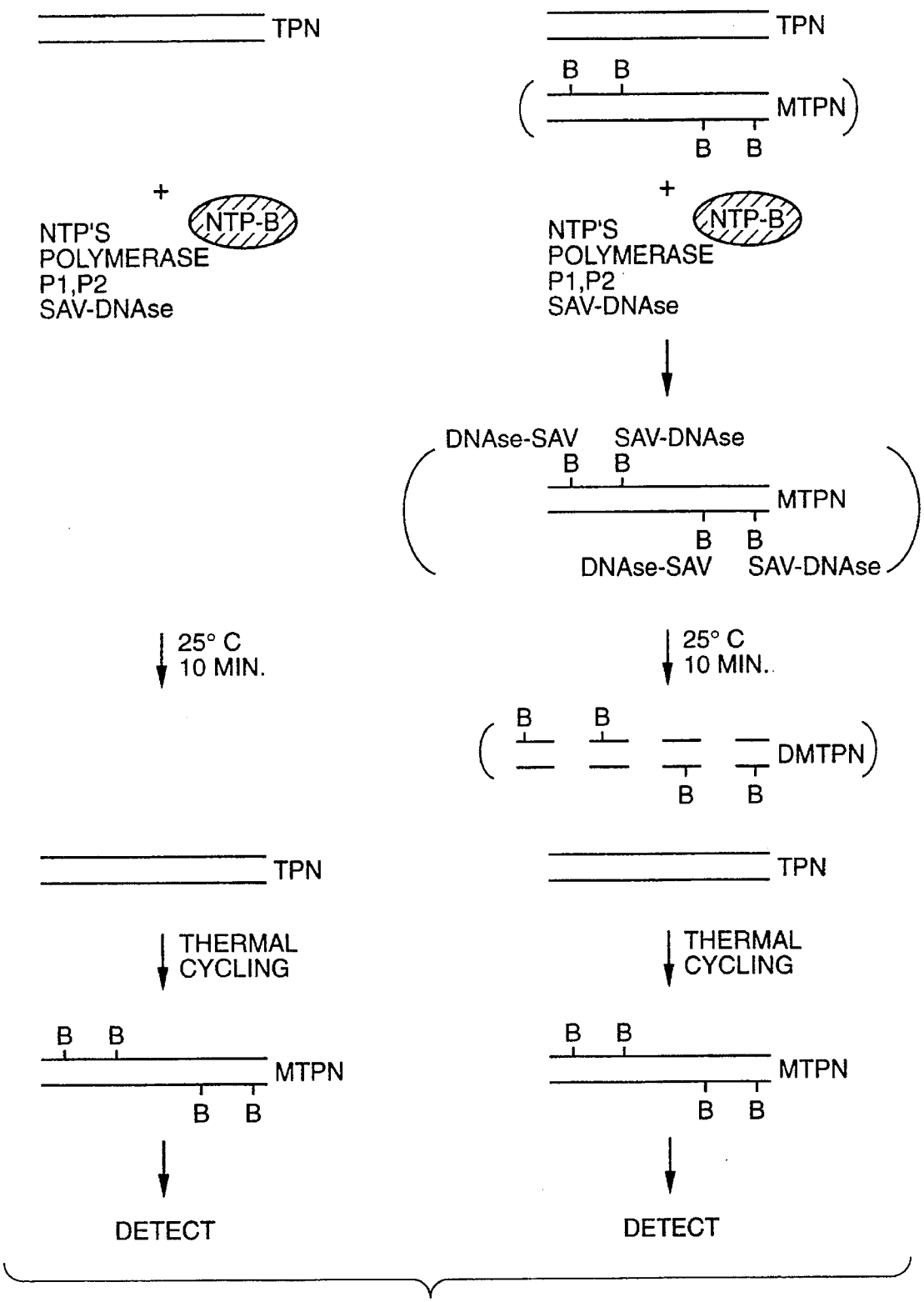
FIG._1

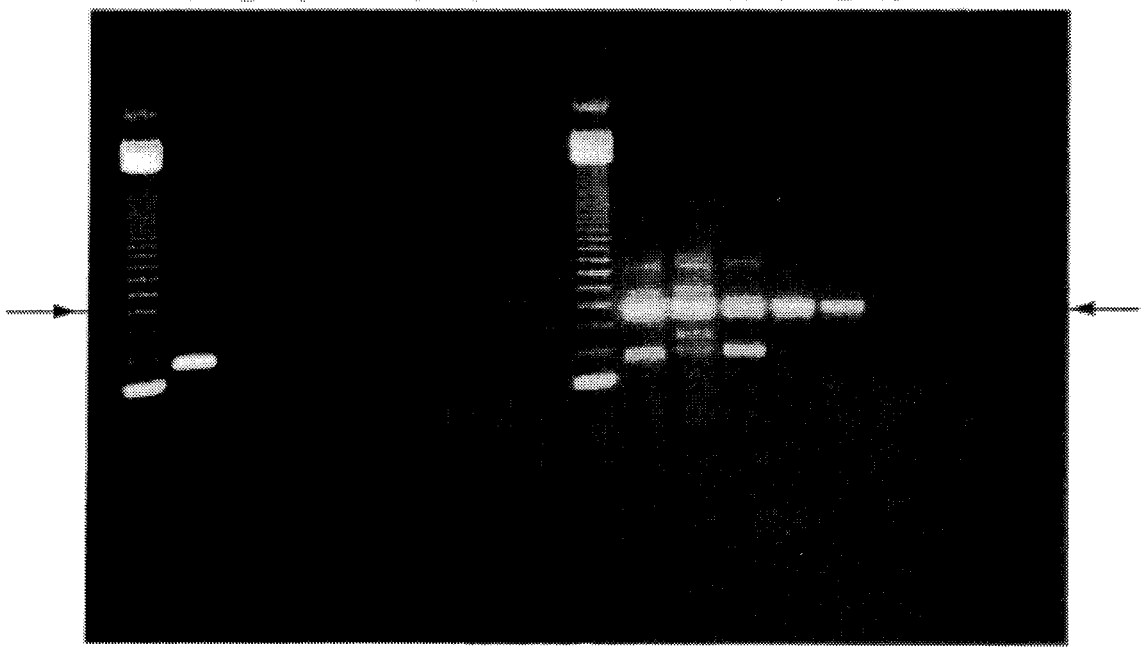
FIG._2
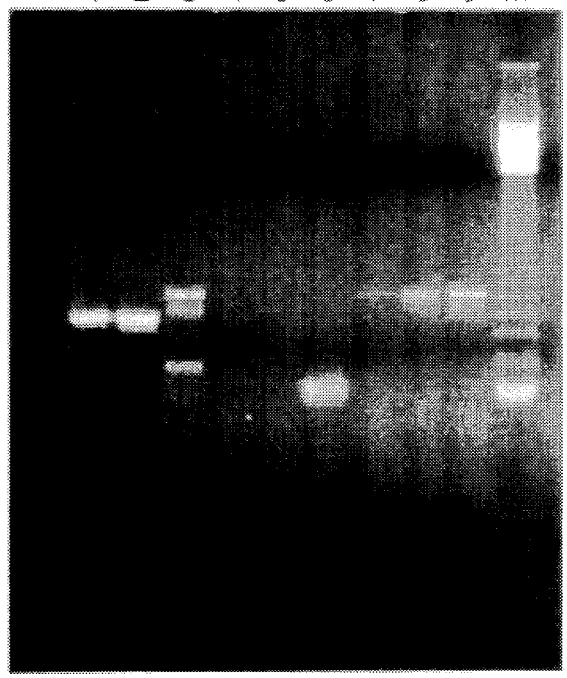
FIG._3

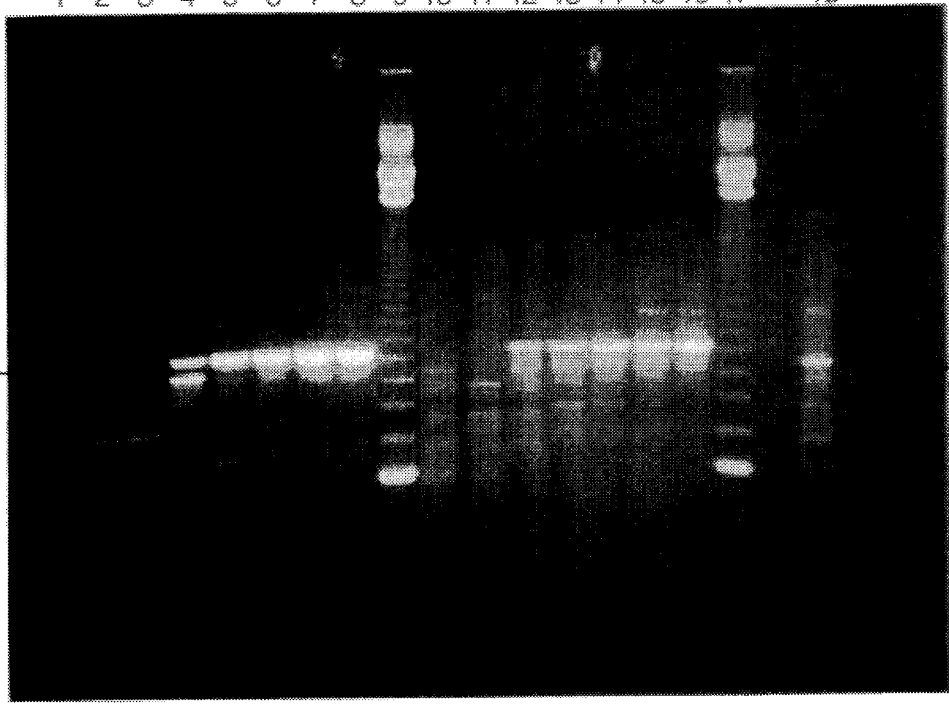
FIG._4
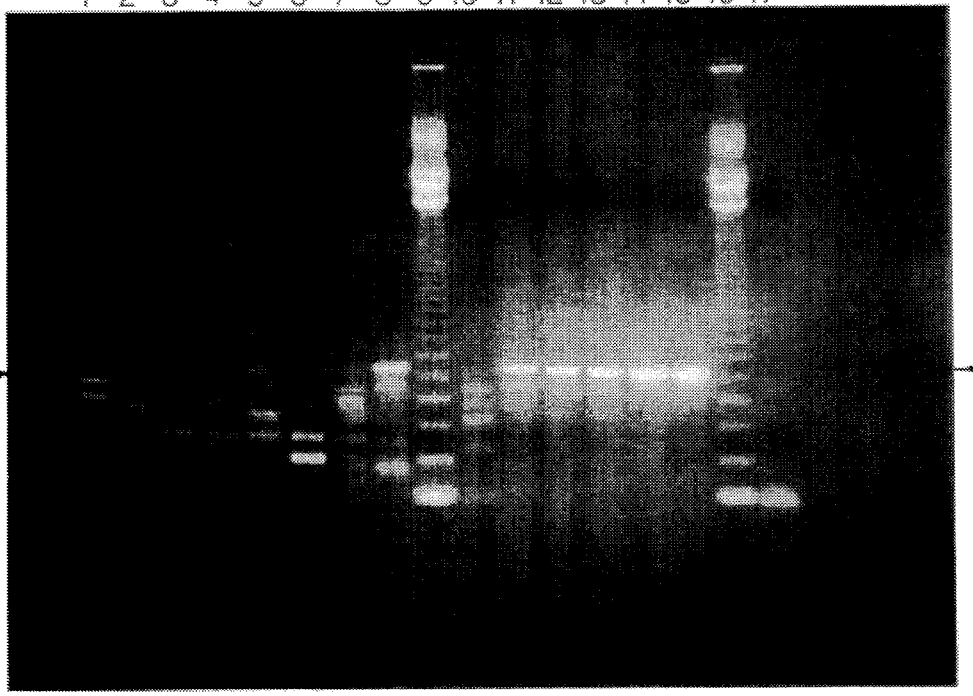
FIG._5

METHOD FOR PREVENTING AMPLIFICATION OF NUCLEIC ACID CONTAMINANTS IN AMPLIFICATION MIXTURES USING NUCLEASE-RECEPTOR CONJUGATES

BACKGROUND OF THE INVENTION

1. Field of the Invention

The present invention relates to methods for producing copies of a nucleic acid and for detecting the presence of polynucleotide analytes. Particularly, the present invention relates to the prevention of amplification of a nucleic acid contaminant from one sample to the next during the above methods.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid or tissue and the unavailability of a sufficiently sensitive method of nucleic acid hybridization analysis.

Recently, a method for the enzymatic amplification of specific double stranded sequences of DNA known as the polymerase chain reaction (PCR) has been described. This in vitro amplification procedure is based on repeated cycles of denaturation, oligonucleotide primer annealing, and primer extension by thermophilic polymerase, resulting in the exponential increase in copies of the desired sequence flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method that has recently been described is an amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may be already part of a polynucleotide analyte or may be created as the result of the presence of a polynucleotide.

Another method for achieving the result of an amplification of nucleic acids is known as the ligase chain reaction (LCR). This method uses a ligase enzyme to join preformed nucleic acid probes. The probes hybridize with the nucleic acid analyte, if present, and ligase is employed to link the probes together resulting in two templates that can serve in the next cycle to reiterate the particular nucleic acid sequence.

Another method for achieving a nucleic acid amplification is the nucleic acid sequence based amplification (NASBA). This method is a primer-directed, enzymatic process that induces in vitro continuous, homogeneous and isothermal amplification of a specific nucleic acid.

Another method for amplifying nucleic acids is the Q-beta-replicase method, which relies on the ability of Q-beta-replicase to amplify a specific RNA substrate exponentially and is used as a label to detect binding rather than a method to create more target nucleic acid.

One method for detecting nucleic acids is to employ nucleic acid probes. One method utilizing such probes is described in U.S. Pat. No. 4,868,104, the disclosure of which is incorporated herein by reference. A nucleic acid probe may be, or may be capable of being, labeled with a reporter group or may be, or may be capable of becoming, bound to a support.

Detection of signal depends upon the nature of the label or reporter group. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

For any of the above methods for amplifying nucleic acid there is a risk of contaminating the amplification mixture with previously amplified material and thereby amplifying material that was not present in the original sample, namely, a contaminant. The quantities of amplification product can be very large thereby aggravating the potential contamination. Once aerosols of amplified nucleic acid are produced in a laboratory, droplets containing this material can invade subsequent amplification mixtures or equipment. Attempted amplification of a nucleic acid may then produce amplified copies of this contaminating material even when the target nucleic acid, or sequence thereof, was not present in the sample being amplified. Such contamination can also occur if the same container is employed for multiple amplifications even though the container is cleaned.

As few as one molecule will sometimes be sufficient to contaminate other containers that are to be used in further amplifications. This possibility for contamination can result in a false test since such a single molecule can be amplified and detected. The result of the test will not accurately reflect the presence or absence of the particular nucleic acid in the patient sample being tested.

Recently, a containment cuvette for amplification of nucleic acids has been disclosed. The cuvette and its method of use are designed to prevent amplified nucleic acid from being released into the atmosphere.

The need still exists for methods for carrying out assays that avoid false positives caused by cross-contamination of samples, are preferably homogeneous and are automatable with relatively simple instrumentation.

2. Description of the Related Art

U.S. Pat. No. 5,035,996 (Hartley) discloses a process for controlling contamination of nucleic acid amplification reactions. An amplification procedure is performed on a first sample in which one or more of the four normal ribonucleoside triphosphates or deoxyribonucleoside triphosphates is replaced with an exo-sample nucleotide. After amplification, any contaminating amplified product that may be remaining is subjected to a physical, chemical, enzymatic, or biological treatment that renders nucleic acid containing the exo-sample nucleotide substantially unamplifiable. The treatment may be done as a separate step or it may be done in the presence of a second sample containing nucleic acid sequences to be amplified. The amplified nucleic acid sequences derived from the first sample which contaminates the second sample are not further substantially amplified during amplification of nucleic acid sequences of the second sample.

International Patent Application No. PCT/US91/03052 discusses a method for reducing carryover contamination in an amplification procedure. The method involves incorporation of at least one modification into the amplification product. A modification is preferably incorporated into an amplification product by using presynthesized amplification probes or primers that contain the selected modification. The modified amplification product is readily distinguishable from the target sequence in a test sample. Prior to amplifying the target in a new test sample, the sample may be treated to selectively eliminate the contaminant amplification product so that it cannot be amplified in the new sample. The modifications may include the introduction of a ligand such as biotin or fluorescein into the contaminant amplification product. The resulting biotin- or fluorescein-modified amplification product can be removed from subsequent test samples by contacting these samples with immobilized avidin or anti-fluorescein antibody, respectively.

Longo, et al., in *Gene* (1990) 93:125–128, describe the use of uracil DNA glycosylase to control carry-over contamination in polymerase chain reactions. The method has two steps: (i) incorporating dUTP in all PCR products (by substituting dUTP for dTTP, or by incorporating uracil during synthesis of the oligodeoxyribonucleoside primers; and (ii) treating all subsequent fully preassembled starting reactions with uracil DNA glycosylase (UDF), followed by thermal inactivation of UDG. UDG cleaves the uracil base from the phosphodiester backbone of uracil-containing DNA, but has no effect on natural (i.e., thymine-containing) DNA. The resulting apyrimidinic sites block replication by DNA polymerases, and are very labile to acid/base hydrolysis. Because UDG does not react with dUTP, and is also inactivated by heat denaturation prior to the actual PCR, carry-over contamination of PCRs can be controlled effectively if the contaminants contain uracils in place of thymines. This method was applied by Pang, et al., in *Molecular and Cellular Probes* (1992) 6:251–156, for the control of contamination in the PCR-based amplification of RNA.

Walder, et al., in *Nucleic Acids Research* (1993) 21(18):4339–4343, discuss the use of PCR primers containing a 3'-terminal ribose residue to prevent cross-contamination of amplified sequences.

Two alternative protocols for pre-PCR sterilization which utilize exonuclease III, which catalyzes the sequential cleavage of 5'-mononucleotides from the 3'-hydroxyl end of duplex DNA, are described by Zhu, et al., in *Nucleic Acids Research* (1991) 19(9):2511.

The use of geometric differences allowing for differential enzymatic inactivation of PCR product and genomic targets in preventing carry-over contamination in PCR is discussed by Muralidhar, et al., *Gene* (1992) 117:107–112.

Cimino, et al., in *Nucleic Acids Research* (1991) 19(1):99–107, disclose a post-PCR sterilization method to control carryover contamination for the polymerase chain reaction. See also Issacs, et al., *Nucleic Acids Research* (1991) 19(1):109–116.

The use of 8-methoxypsoralen and long-wave UV light to eliminate contaminating DNA in polymerase chain reaction reagents is described by Meier, et al., in *Journal of Clinical Microbiology* (1993) 31(3):646–652. The use of ultraviolet light alone to eliminate sources of contamination in PCR is discussed by Sarkar, et al., in *Nature* (1990) 346:27.

Furrer, et al., in *Nature* (1990) 343:324, describe treatment of individual reaction mixtures in PCR, before adding template DNA and Taq polymerase, with DNaseI or restriction endonucleases that cut internal to the pair of amplification primers to prevent amplification of contaminating DNA.

PCT Patent Application No. PCT/FR91/00513 (Brandys, et al.) discloses an improvement to the method of in vitro enzymatic amplification (PCR method) of a target DNA sequence present in heterologous DNA in a medium that comprises a DNA polymerase and a primer oligonucleotide. The method includes various cyclically repeated amplification steps whereby, at a chosen time following the end of the amplification cycles, the resulting amplification products are made unsuitable for later reamplification and/or before the start of the PCR reaction, a pretreatment is carried out to selectively prevent any reamplification of the previous amplification products resulting from a PCR reaction using the same primer oligonucleotides.

Corey, et al., in *Biochemistry* (1989) 28(21):8277–8286 disclose the generation of a catalytic sequence-specific hybrid DNase.

Biotinylated dUTP is discussed by Lo, et al., "PCR Protocols: A Guide to Methods and Applications" (1990) Academic Press, San Diego, Calif..

A containment cuvette for conducting PCR is disclosed in European Patent Application publication number 0 381 501 (Schnipelsky, et al.). Detection reagents are either pre-incorporated into compartments in the cuvette or are added after amplification. In the latter situation a check valve prevents amplified nucleic acid from being released. Transfer of liquids between compartments is achieved by the use of flexible compartment walls and an external pressure source or by pistons that are part of the cuvette and operate on the compartments as a piston within a piston chamber.

A device for processing biological specimens for analysis of nucleic acids is described in U.S. Pat. No. 5,188,963. The device has a hinged compartment facilitating automation of DNA- and RNA-based diagnostics and genetic surveillance and detection. Specimens are embedded in a matrix in the carrier. The matrix is then treated by one or more of the techniques such as amplification, electrophoresis, and hybridization as selected for the desired analysis and then the sample is treated to detect the cellular component.

A process for amplifying, detecting and/or cloning nucleic acid sequences otherwise referred to as PCR is disclosed in U.S. Pat. Nos. 5,008,182, 4,965,188, 4,800,159, 4,683,195 and 4,683,202. Sequence polymerization by PCR is described by Saiki, et al., (1986) *Science*, 230: 1350–1354.

U.S. patent application Ser. Nos. 07/299,282, abandoned and 07/399,795, abandoned, filed Jan. 19, 1989, and Aug. 29, 1989, respectively, describe nucleic acid amplification using a single polynucleotide primer. U.S. patent application Ser. No. 07/555,323 filed Jul. 19, 1990, discloses methods for producing a polynucleotide for use in single primer amplification. U.S. patent application Ser. No. 07/555,968 filed Jul. 19, 1990 U.S. Pat. No. 5,439,793, describes a method for producing a molecule containing an intramolecular base-pair structure. U.S. patent application Ser. No. 07/776,538 filed Oct. 11, 1991, abandoned, discloses methods for producing a polynucleotide for use in single primer amplification. U.S. patent application Ser. No. 07/923,079 filed Jul. 31, 1992 abandoned, describes a method for introducing sequences at the 3' end of polynucleotides. The disclosures of these six applications are incorporated herein by reference in their entirety.

Other methods of achieving the result of a nucleic acid amplification are described by Van Brunt in *Bio/Technolgy* (1990) 8(No.4): 291–294. These methods include ligase chain reaction (LCR), nucleic acid sequence based amplification (NASBA) and Q-beta-replicase amplification of RNA. LCR is also discussed in European Patent Applications Nos. 439,182 (Backman I) and 473,155 (Backman II).

SUMMARY OF THE PRESENT INVENTION

One aspect of the present invention is a method of preventing amplification of a nucleic acid contaminant in amplification of a nucleic acid suspected of being present in a sample. Modified nucleotides that render copies of the nucleic acid bindable by a member of a specific binding pair, such as a receptor, which does not bind to the nucleic acid, are incorporated into copies of the nucleic acid that are produced during the amplification. The sample is combined with a enzyme conjugate, usually a receptor bound to a nuclease, under conditions wherein prior to the amplification the member of a specific binding pair binds to the copies and the enzyme degrades the copies but not the nucleic acid. The modified nucleotides generally are incorporated into the copies of the nucleic acid during the amplification reaction by use of modified nucleoside triphosphates and/or a modified oligonucleotide.

Another aspect of the present invention is a method for conducting amplification of a nucleic acid. In the method a combination is provided containing a sample suspected of containing a nucleic acid and a conjugate comprising a nuclease, such as a DNAse, and a receptor that binds to a modified nucleotide in copies of the nucleic acid and not to the nucleic acid itself. The method also utilizes reagents for conducting an amplification of the nucleic acid, wherein the reagents include at least one modified nucleoside triphosphate for incorporation as a modified nucleotide into copies of the nucleic acid during the amplification and/or at least one modified oligonucleotide such as a modified polynucleotide primer for incorporation into copies of the nucleic acid. If the modified nucleoside triphosphate or the modified oligonucleotide is present in the initial combination, the modified material is normally present in a protected form, from which the modified material is subsequently released. Otherwise, the modified material is added after the step of the method in which the combination is subjected to conditions wherein the receptor binds to the modified nucleotide in the copies and the nuclease degrades the copies without degrading the nucleic acid. The combination is then subjected to conditions wherein the nucleic acid is amplified.

Another aspect of the present invention is a method for preparing copies of a nucleic acid. A sample suspected of containing a nucleic acid is combined with DNA polymerase, at least one oligonucleotide, and a conjugate comprising a DNAse and receptor that binds to copies of the nucleic acid containing a modified nucleotide and not to the nucleic acid. The combination is subjected to a temperature of 0° C. to 40° C. for a period of 1 to 60 minutes during which the receptor binds to the copies and the DNAse degrades the copies without degrading the nucleic acid. Also employed are deoxyribonucleoside triphosphates such as those selected from the group consisting of dATP, dCTP, dGTP and dTTP, and at least one modified deoxyribonucleoside triphosphate for incorporation into copies of the nucleic acid. The modified deoxyribonucleoside triphosphate is in a protected form if present prior to step (b) or is added after step (b). The temperature of the combination is then changed repeatedly by at least 10° C. within the range of 50° C. to 100° C., such as by repeatedly alternating the temperature between 40° C. to 8° C. and 60° C. to 100° C.

Another aspect of the present invention is a method for determining the presence of a polynucleotide analyte, which is a nucleic acid. In the method a sample suspected of containing a polynucleotide analyte is combined with DNA polymerase and a conjugate comprising a DNAse and receptor that binds to the copies and not to said nucleic acid. The combination is subjected to an incubation at a temperature of 0° C. to 40° C. for a period of 1 to 60 minutes to allow the receptor to bind to the copies and the DNAse to degrade the copies without degrading the polynucleotide analyte. Additional reagents for conducting an amplification include nucleoside triphosphates and at least one oligonucleotide primer, wherein at least one of the nucleoside triphosphates is modified and/or the oligonucleotide primer is modified for incorporation of a modified nucleotide into copies of the nucleic acid during the amplification. The modified reagents are present either in the combination prior to the above incubation in a protected form or they are added after the incubation. Then, the temperature of the combination is repeatedly alternated between 40° C. to 80° C. and 60° C. to 100° C., which releases the modified reagents from the protected form, if the modified reagents are in the initial combination, and permits amplification of the nucleic acid. Copies of the polynucleotide analyte are detected.

Another aspect of the present invention is a method of preventing carry-over contamination in amplification of a nucleic acid suspected of being present in a plurality of samples. The method comprises (a) during amplification of the first of the samples containing the nucleic acid, incorporating, into copies of the nucleic acid that are produced during the amplification, modified nucleotides that render the copies bindable by a receptor that does not bind to the nucleic acid and (b) prior to subjecting the remainder of the samples to amplification, combining each of the samples with a receptor bound to a nuclease, under conditions wherein the receptor binds to the copies and the nuclease degrades the copies but not the nucleic acid.

The present invention also encompasses a kit comprising in packaged combination (a) nucleoside triphosphates such as deoxyribonucleoside triphosphates or ribonucleoside triphosphates wherein one of the nucleoside triphosphates is modified, (b) polynucleotide polymerase, (c) at least one polynucleotide primer, and (d) a conjugate comprising a DNAse and receptor that binds to an amplified nucleic acid produced from the modified nucleoside triphosphate wherein the receptor does not bind to the nucleic acid.

Another aspect of the present invention is a kit for amplifying a nucleic acid comprising in packaged combination a conjugate of a receptor and a nuclease, an oligonucleotide, and nucleoside triphosphates, wherein at least one of the nucleoside triphosphates and the oligonucleotide is modified and wherein the receptor binds to amplified nucleic acid produced from the modified nucleoside triphosphates and the oligonucleotide and not to the nucleic acid.

BRIEF DESCRIPTION OF THE DRAWINGS

FIG. 1 is a schematic depicting an embodiment of the present invention.

FIGS. 2, 3 and 5 are photographs of agarose gels produced in experiments in accordance with the present invention.

FIG. 4 is a photograph of an agarose gel produced in a control experiment.

DESCRIPTION OF THE SPECIFIC EMBODIMENTS

As mentioned above, the present invention provides methods for conducting nucleic acid amplification reactions. The present invention is particularly useful for an assay of nucleic acids used in conjunction with an amplification procedure.

The present methods differ from known methods in several important ways. For example, the present method can utilize an analog of any of the bases rather than a specific base, such as deoxyuracil triphosphate. In addition, the present method is applicable not only to the amplification of DNA but also to the amplification of RNA as well. Furthermore, the present invention is not restricted to any particular enzyme; rather, the requirement for the enzyme is that it be capable of modifying the nucleic acid in such a way that the nucleic acid can no longer be amplified. Also, it is not necessary in the present invention to perform a separation step in order to remove the contaminant from the amplification medium.

Before proceeding further with a description of the specific embodiments of the present invention, a number of terms will be defined.

Nucleic acid or polynucleotide analyte—a compound or composition to be measured that is a polymeric nucleotide or a portion of a polymeric nucleotide, which in the intact natural state can have about 200 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation of the polymeric nucleotide. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological materials by procedures well-known in the art. Some examples of such biological material by way of illustration and not limitation are disclosed in Table I of U.S. patent application Ser. No. 07/923,079 filed Jul. 31, 1992 abandoned, which Table I is incorporated herein by reference.

The polynucleotide analyte, where appropriate, may be treated to cleave the analyte to obtain a polynucleotide fragment that contains a target polynucleotide sequence. Such cleaving treatments may be accomplished, for example, by shearing or by treatment with a restriction endonuclease or other site specific chemical cleavage method. However, it is an advantage of the present invention that the polynucleotide analyte can be used in its isolated state without further cleavage. The cleaved and uncleaved polynucleotide fragments may each be referred to herein as a polynucleotide analyte.

For purposes of this invention, the polynucleotide analyte, or a cleaved fragment obtained from the polynucleotide analyte, may be at least partially denatured or single stranded or treated to render it denatured or single stranded. Such treatments are well-known in the art and include, for instance, heat or alkali treatment. For example, double stranded DNA, when heated at 90°–100° C. for a period of 10–20 seconds or more, produces denatured material.

Sample—the material suspected of containing the nucleic acid analyte. Such samples include biological fluids such as blood, serum, plasma, sputum, lymphatic fluid, semen, vaginal mucus, feces, urine, spinal fluid, and the like; biological tissue such as hair and skin; and so forth. Other samples include cell cultures and the like, plants, food, forensic samples such as paper, fabrics and scrapings, water, sewage, medicinals, etc.. The sample may be pretreated with reagents to liquefy the sample and release the nucleic acids from binding substances. Such pretreatments are well-known in the art.

Oligonucleotide—a polynucleotide, usually a synthetic polynucleotide, usually single stranded and selected in view of the known sequence of a polynucleotide analyte depending on the type of amplification to be conducted. The oligonucleotide(s) are usually comprised of a sequence of at least 10 nucleotides, preferably, 20 to 90 nucleotides, more preferably, 15 to 50 nucleotides.

Various well-known techniques can be employed for preparing oligonucleotides. Such sequences can be obtained by biological synthesis or by chemical synthesis. For short sequences (up to about 100 nucleotides) chemical synthesis is frequently more economical as compared to biological synthesis. For longer sequences standard replication methods employed in molecular biology can be used such as the use of M13 for single stranded DNA as described by J. Messing, *Methods Enzymol* (1983) 101: 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol* (1979) 68: 90) and synthesis on a support (Beaucage, et al., *Tetrahedron* (1981) *Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Polynucleotide primer(s) or oligonucleotide primer(s) —an oligonucleotide that is usually employed in a chain extension on a polynucleotide template such as in, for example, an amplification of a nucleic acid.

Modified polynucleotide primer or modified oligonucleotide primer—an oligonucleotide that contains at least one, and preferably three or more, modified nucleotides. The modified nucleotide(s) may be present in the oligonucleotide at any position other than that which would render such modified oligonucleotide inoperable in an amplification. For PCR the modified nucleotide(s) should not be at the 3'-end unless such modified nucleotide would be extendable in an amplification. In an LCR the modified nucleotide(s) should not be at an end that is contiguous with the end of another oligonucleotide used in LCR. Procedures for preparing oligonucleotides are known in the art and are discussed above. Such procedures can be easily adjusted for the preparation of oligonucleotides having a modified nucleotide(s). One such method involves the introduction of an amine group into the oligonucleotide. Following coupling, oxidation and deprotection the modifying group can be attached.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar. The purine bases include adenine(A), guanine(G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP and rUTP.

Modified nucleoside triphosphate—derivative or analog of a nucleoside triphosphate which can function as a substrate of a polymerase enzyme and be incorporated into a polynucleotide through catalysis by such enzyme. The derivatives and analogs are exemplified by those that are recognized and polymerized by the enzyme in a similar manner to the underivatized nucleoside triphosphates. Examples of such derivatives or analogs by way of illustration and not limitation include those nucleoside triphosphates covalently bound to a member of a specific binding pair or bound to a substituent that renders the resultant compound a member of a specific binding pair or at least bindable by another molecule. Generally, the member of a specific binding pair is of a size that minimizes any reduction in the incorporation of the modified nucleoside triphosphate into the copies of nucleic acid produced during an amplification. Examples of modified nucleoside triphosphates, by way of illustration and not limitation, are deoxyribonucleoside triphosphates alkylated with alkyl chains or radicals having from 1–20 carbon atoms, preferably, 1–5 carbon atoms, halogenated (chlorine, bromine, iodine) deoxyribonucleoside triphosphates and deoxyribonucleoside triphosphates that are covalently bound to a small organic molecule or ligand generally having a molecular weight of about 50 to 2000, preferably 100 to 1500, such as, for example, haptens, e.g., fluorescein, digoxin, dinitrophenyl, fluorene and the like, biotin and vitamin B12. The small organic molecule or ligand should be one for which a complementary specific binding pair member, e.g., receptor, is available. Typical sites for substitution on a pyrimidine or purine ring are designated below by an asterisk:

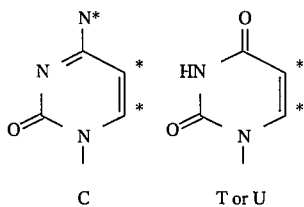

C          T or U

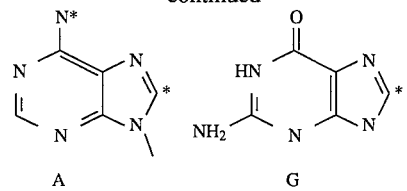

A          G

In addition, N in the 7 position of the purine can be replaced by C-R, where R is a substituent.

Such derivatives and analogs can be prepared by procedures based upon known procedures such as those involving chemical and enzymatic syntheses. Such procedures are described, for example, by Engelhardt, et al., in European Patent Application 0302175A2 published Feb. 8, 1989, and by Dattagupta, et al., in U.S. Pat. No. 4,808,520 issued Feb. 28, 1989, the relevant portions of which are incorporated herein by reference. The derivatives and analogs must be prepared in a manner that does not prevent the modified nucleoside triphosphate from becoming incorporated into the amplified nucleic acid.

For example, DNA can be methylated by using a methylase such as that from *E. coli*, e.g., dam methylase and dcm methylase. See, for example, "Molecular Cloning-A Laboratory Manual," second edition, J. Sambrook, et al., published by Cold Spring Harbor Laboratory Press, (1989), page 5.15. Other alkylated deoxyribonucleoside triphosphates can be prepared in a similar manner.

Some halogenated deoxyribonucleoside triphosphates are commercially available, such as for example, 5-bromouridine and others can be prepared by techniques that are known in the literature or by procedures based upon the above techniques.

In general, a ligand must be attached to the deoxyribonucleoside triphosphate in a manner that does not prevent the modified nucleoside triphosphate from becoming incorporated into amplified nucleic acid. Biotinylated deoxyribonucleoside triphosphates, for example, can be prepared by a procedure similar to that described by Langer, et al., in the *Proc. Natl Acad. Sci USA* (1981) 78(11):6633–6637 entitled "Enzymatic synthesis of biotin-labeled polynucleotides: Novel nucleic acid affinity probes." In Langer, analogs of dUTP and UTP that contain a biotin molecule covalently bound to the C-5 position of the pyrimidine ring through an allylamine linker arm were synthesized. In a similar manner biotin can be attached to dUTP at other positions and also can be attached to other deoxyribonucleoside triphosphates such as dATP, dCTP, dGTP and dTTP and also ribonucleoside triphosphates. Other nucleoside triphosphate-ligand compounds can be prepared by diazo coupling to the 8'-position of purines, mercuration of the 5'-position of uridine (Bergstrom and Ruth, *J. Carbohydrates, Nucleosides and Nucleotides,* (1977), 4(5):257), alkylation of an amine group of cytidine, adenosine or guanosine, for example, the 4'-amine of cytosine (Gebeyehu, et al., U.S. Pat. No. 4,828, 979), bromination of the 5'-position of uridine, the use of 3,4-disubstituted and 3,4,6,-trisubstituted pyrazolo[3,4-d] pyrimidines as described by Petrie, et al., in WO 90/03370 in place of conventional nucleotides such as T and G.

If the modified nucleoside or modified oligonucleotide is to be present with the enzyme conjugate, it is convenient to have the modified material in a protected form. In one approach a ligand precursor is employed. The precursor is usually designed to prevent the modified nucleoside triphosphate or the modified oligonucleotide from binding to the conjugate comprising an enzyme and a specific binding pair member complementary to the ligand, such as a receptor for the ligand. Preferably, the precursor is converted to the ligand on heating to less than 99 C. The use of such a precursor allows the modified material and the conjugate to be present together in the amplification mixture. The precursor can contain any group that is removed on heating and that effectively prevents binding by the receptor of the enzyme-receptor conjugate.

One example of such precursors with respect to biotin is a substituted silane, e.g., alkyl silyl such as t-butyl-dimethyl silyl, which is bound to one of the nitrogen atoms of biotin according to known procedures. On heating or treatment with fluoride ion or both, the substituted silane group is removed. Other biotin precursors that behave in a similar manner have a methyl formyl or a benzene sulfonyl methylene group at one of the nitrogen atoms of biotin while other such biotin precursors have a benzyl or a dimethylphosphate at the oxygen atom of biotin in the form of an oxime.

Those skilled in the art will appreciate that other removable protective groups may be employed such as, for example, carbamates (amine groups), esters (carboxylic acid groups), alpha-carboxy ketones (ester groups), xanthates (double bonds), sulfates (alcohols), and so forth. Other examples include addition of fumaric acid to dienes to give cyclohexene adducts, azide reaction with alkyl halides to give alkyl azides, production of alkyl/aryl sulfides from mercaptans, addition of mercaptans to alpha, beta-unsaturated sulfones to give sulfides, hydrolization of alkylsulfonates to give alcohols, and the like. In another approach the ligand bound to the nucleoside triphosphate can be treated with an antibody for the ligand to form a complex, which will render the ligand non-reactive. At the appropriate time heat can be applied to destroy the antibody rendering the ligand reactive to its complementary receptor.

Where a ligand precursor is not used, it is usually necessary to provide a way to introduce the modified nucleoside triphosphate or the modified oligonucleotide after any amplified nucleic acid contaminant has been destroyed. If this is not done, the receptor will combine with the modified nucleoside triphosphate or modified oligonucleotide and less will be available to react with the contaminating nucleic acid. Accordingly, the modified nucleoside triphosphate or the modified oligonucleotide can be included in the reaction mixture in a protected (non-reactive) form such as incorporated in wax or a low melting polymer from which it can be released on heating.

Contaminant—a polynucleotide containing at least one modified nucleotide and comprised of a sequence contained in the nucleic acid analyte, such polynucleotide being exogenous to the sample to be analyzed. Without removal or destruction or incapacitation of such polynucleotide, the contaminant is amplified during the amplification carried out for the amplification for a polynucleotide analyte suspected of being in such sample. Usually, the contaminant results from a previous amplification and is carried over into a subsequent amplification either by aerosol formation or by its presence in the amplification device. The contaminant may be present in one or a few molecules up to many thousands of molecules depending on a number of factors such as the number of molecules of nucleic acid produced in the previous amplification.

Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during an amplification reaction and therefore becoming part of the nucleic acid polymer.

Nucleoside—is a base-sugar combination or a nucleotide lacking a phosphate moiety.

Amplification of nucleic acids or polynucleotides—any method that results in the formation of one or more copies of a nucleic acid or a polynucleotide molecule, usually a nucleic acid or polynucleotide analyte, present in a medium. One such method for the enzymatic amplification of specific double stranded sequences of DNA is known as the polymerase chain reaction (PCR), as described above. This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is mentioned above and involves amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may be already part of a polynucleotide analyte or may be created as the result of the presence of a polynucleotide.

Another method for achieving the result of an amplification of nucleic acids is known as the ligase chain reaction (LCR). This method uses a ligase enzyme to join preformed nucleic acid probes. The probes hybridize with the nucleic acid analyte, if present, and ligase is employed to bind the probes together resulting in two templates that can serve in the next cycle to reiterate the particular nucleic acid sequence.

Another method for achieving a nucleic acid amplification is the nucleic acid sequence based amplification (NASBA). This method is promoter-directed, enzymatic process that induces in vitro continuous, homogeneous and isothermal amplification of specific nucleic acid.

Another method for amplifying a specific group of nucleic acids is the Q-beta-replicase method, which relies on the ability of Q-beta-replicase to amplify its RNA substrate exponentially.

Another method for conducting an amplification of nucleic acids is referred to as strand displacement amplification (SDA). SDA is an isothermal, in vitro DNA amplification technique based on the ability of a restriction enzyme to nick the unmodified strand of a hemiphosphorothioate form of its restriction site and the ability of a DNA polymerase to initiate replication at the nick and displace the downstream nontemplate strand intact. Primers containing the recognition sites for the nicking restriction enzyme drive the exponential amplification.

Another amplification procedure for amplifying nucleic acids is known as 3SR, which is an RNA specific target method whereby RNA is amplified in an isothermal process combining promoter directed RNA polymerase, reverse transcriptase and RNase H with target RNA.

Conditions for carrying out an amplification, thus, vary depending upon which method is selected. Some of the methods such as PCR utilize temperature cycling to achieve denaturation of duplexes, oligonucleotide primer annealing, and primer extension by thermophilic template dependent polynucleotide polymerase. Other methods are isothermal. As can be seen, there are a variety of known amplification methods and a variety of conditions under which these methods are conducted to achieve amplification. The present invention can be applied to all such amplification reactions.

Polynucleotide polymerase—a catalyst, usually an enzyme, for forming an extension of the polynucleotide primer along a nucleic acid template that is comprised predominantly of deoxynucleotides. The polydeoxynucleotide polymerase is a template dependent polydeoxynucleotide polymerase and utilizes the nucleoside triphosphates as building blocks for extending the 3' end of the polynucleotide primer to provide a sequence complementary with a single stranded polynucleotide sequence. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase (Vent is a trademark of New England BioLabs, Beverly, Mass.), Pfu DNA polymerase, Taq DNA polymerase, and the like, derived from any source such as cells, bacteria, for example, E. coli, plants, animals, virus, thermophilic bacteria, and so forth. Where the target polynucleotide sequence is RNA, reverse transcriptase is used as at least one of the polynucleotide polymerases to facilitate extension of the primer along the complementary strands of the polynucleotide analyte.

Hybridization (hybridizing) and binding—in the context of nucleotide sequences these terms are used interchangeably herein. The ability of two polynucleotide sequences to hybridize with each other is based in a large part on the degree of complementarity of the two polynucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Another factor to be considered is the nature of the nucleotide pairs that are opposite in the two strands. Some nucleotide pairs, such as G and C, have greater binding affinities for one another than do other pairs. Increased stringency is achieved by elevating the temperature, increasing the ratio of cosolvents, lowering the salt concentration, and the like.

Homologous or substantially identical—In general, two polynucleotide sequences that are identical, or at least can each hybridize to the same polynucleotide sequence, are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—two sequences are complementary when the sequence of one can bind to the sequence of the other in an anti-parallel sense wherein the 3' end of each sequence binds to the 5' end of the other sequence and, for example, among the natural bases each A, T(U), G, and C of one sequence is then aligned with a T(U), A, C, and G, respectively, of the other sequence.

Copy—a sequence that is identical to or homologous with a single stranded polynucleotide sequence as differentiated from a sequence that is complementary to or hybridizable with the sequence of such single stranded polynucleotide.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared. Preferred ligands are small organic molecules.

Small organic molecule—a compound of molecular weight less than 2000, preferably 100 to 1500, such as vitamin B12, biotin, haptens such as fluorescein, rhodamine and other dyes, tetracycline and other protein binding molecules, etc.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, intrinsic factor, folate binding protein, cyclophilin, and the like, antibodies (monoclonal and polyclonal), avidin, streptavidin, enzymes, Fab fragments, lectins, nucleic acids, repressors, protection enzymes, protein A, complement component C1q, DNA binding proteins or ligands and the like.

Enzyme for degrading a nucleic acid—a catalyst capable of modifying a nucleic acid in a manner that prevents it from being amplified in an amplification reaction. Usually, the enzyme is capable of promoting the degradation of a nucleic acid or polynucleotide. Preferably, the enzyme is a nuclease.

Nuclease—an enzyme capable of degrading polynucleotides when a conjugate of such nuclease and an sbp member binds to a polynucleotide in accordance with the present invention. The nucleases include endonucleases and exonucleases, preferably endonucleases. For purposes of the present invention the nuclease acts to degrade the polynucleotide either specifically or non-specifically by cleaving bonds either between, or at, the ends of the polynucleotide. The nuclease can degrade double stranded (e.g., DNA) or single stranded polynucleotides (DNA or RNA) or both. Examples of nucleases that can be used in the present invention, by way of illustration and not limitation, are deoxyribonucleases (DNases) such as DNase I, which hydrolyzes double-stranded or single-stranded DNA preferentially at sites adjacent to pyrimidine nucleotides, ribonucleases (RNases), restriction endocleases such as types I, II and III, N. crassa endonuclease, S1 endonuclease, restriction exonucleases, single stranded and double stranded DNA exonucleases.

The nuclease can be derived from any source such as cells, bacteria, for example, E. coli, Salmonella typhimurium, Haemophilus influenzae, Bacillus subtilis and the like, plants, animals, viruses, and so forth.

Linking Group—a portion of a structure which connects 2 or more substructures. A linking group has at least 1 uninterrupted chain of atoms extending between the substructures. The atoms of a linking group are themselves connected by chemical bonds. The number of atoms in a linking group is determined by counting the atoms in the linking group other than hydrogen. Functional groups used for linking are, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like.

Enzyme conjugate—a molecule comprised of two substructures bound together, either directly or optionally through a linking group and further optionally through a particle, to form a single structure. The binding can be made either by a direct connection (e.g. a chemical bond) between the subunits or by use of a linking group and/or a particle. Within the context of the present invention, an enzyme conjugate has as its substructures an enzyme for degrading a nucleic acid and a member of a specific binding pair. The single structure formed may contain from 1 to 20 molecules of enzyme and from 1 to 20 molecules of sbp member, usually, from 1 to 10 molecules of enzyme and from 1 to 10 molecules of sbp member depending on the size of the sbp member where the number of molecules of enzyme are generally less, the larger the size of the sbp member. In the case of a particle the enzyme conjugate may contain from 1000 to 1500 molecules of enzyme and from 1500 to 2000 molecules of sbp member, usually, from 1200 to 1300 molecules of enzyme and from 1800 to 2000 molecules of sbp member depending on the size of the particle. For purposes of the present invention the enzyme conjugate must be capable of binding to any previously amplified nucleic acid contaminant, must be capable of modifying the nucleic acid contaminant to which it is bound in a manner that prevents the nucleic acid contaminant from being amplified in an amplification reaction, and must be capable of being deactivated. Usually, deactivation will be accomplished by heating to a temperature of less than 99° C., preferably, 50°–90° C., for a period of 5 seconds to 1 hour, preferably, 5 seconds to 5 minutes. Alternatively, the conjugate can be deactivated by a reagent that is included in the amplification mixture. The reagent can be added before or after deactivation of the contaminant provided that, if added before, modification of the nucleic acid must proceed sufficiently rapidly so that it is complete before the conjugate is deactivated. Reagents useful for deactivation of the conjugate include an enzyme such as a protease, a specific binding partner of the member of the specific binding pair in the conjugate, an inhibitor of the enzyme in the conjugate, or other reagents such as detergents and denaturants or chemical modifiers that can deactivate the conjugate.

Preferred enzyme conjugates are those comprising a nuclease as the enzyme and a receptor for a ligand that is part of the modified nucleotide.

Conjugation—any process wherein two compounds that form a substructure of a conjugate are linked together to form such conjugate. The conjugation process can be comprised of any number of steps. Conjugation of members of a specific binding pair to an enzyme may be accomplished in a number of well-known techniques commonly available in the literature. For example, binding of sbp members to enzymes is described in "Immobilized Enzymes," Ichiro Chibata, Halsted Press, New York (1978) and Cuatrecasas, *J. Biol. Chem.*, 245:3059 (1970). As mentioned hereinbelow, it is not necessarily detrimental in the present invention that the conjugation of the enzyme with the sbp member result in a decrease in catalytic activity of the enzyme.

Label or reporter group or reporter molecule—a member of the signal producing system. Usually the label or reporter group or molecule is conjugated to or becomes bound to a polynucleotide probe or a polynucleotide primer and is capable of being detected directly, or indirectly by being bound through a specific binding reaction, to a detectable substance. Labels able to be detected indirectly include polynucleotides such as a polynucleotide primer or a specific polynucleotide sequence that can act as a ligand for a complementary polynucleotide or provide a template for amplification or ligation or act as a ligand such as for a repressor protein; haptens; antibodies; receptors such as avidin; ligands such as biotin and the like. Labels able to be detected directly may be isotopic or nonisotopic, usually non-isotopic, and can be a catalyst, such as an enzyme, ribozyme, a substrate for a replicase such as QB replicase, promoter, dye, fluorescent molecule, photosensitizer, chemiluminescer, coenzyme, enzyme substrate, radioactive group, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence. Methods for binding of labels to nucleotides are well-known and described, for example, in U.S. Pat. No. 4,948,882 (Ruth), U.S. Pat. No. 5,082,830 (Brakel, et al.), U.S. Pat. No. 4,894,325 (Koser, et al.) and U.S. Pat. No. 4,987,065 (Stavrianopolis, et al.).

Signal Producing System—The signal producing system may have one or more components, at least one component being the label or reporter group. The signal producing system generates a signal that relates to the presence or amount of nucleic acid analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, photosensitizers, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, such as detection of electromagnetic radiation, desirably by visual examination. The signal-producing system is described more fully in U.S. patent application Ser. No. 07/555,323, filed Jul. 19, 1990, the relevant disclosure of which is incorporated herein by reference.

Ancillary Materials—Various ancillary materials will frequently be employed in the method in accordance with the present invention. For example, buffers will normally be present in the medium, as well as stabilizers for the medium and the reaction components. Frequently, in addition to these additives, proteins may be included, such as albumins, nucleic acids such as genomic DNA, organic solvents such as formamide, quaternary ammonium salts, polyanions such as dextran sulfate, surfactants, particularly non-ionic surfactants, binding enhancers, e.g., polyalkylene glycols, or the like.

One aspect of the present invention will now be described in more detail with reference to FIG. 1. Appropriate reaction conditions are chosen for carrying out the modification of any contaminant in accordance with the present invention as well as an amplification reaction. Generally, the contaminant that contains a modified nucleotide in accordance with the present invention is produced in a previous amplification reaction, which may be the first of such amplification reactions conducted on a sample, by incorporating the modified nucleotide into copies of the nucleic acid during the amplification. Usually, the modification of the contaminant and the amplification are conducted as parts of one reaction scheme, which is the same for all of the samples to be analyzed including the first of such samples. In accordance with the present invention a combination is provided that contains a sample (sample 1) suspected of containing a target nucleic acid TPN, reagents for conducting an amplification of the nucleic acid (NTP's and NTP-B wherein the NTP's are dATP, dCTP, dGTP and dTTP and the NTP-B is one of the above covalently linked to biotin) and an enzyme conjugate, for example, a conjugate of a nuclease and a receptor such as streptavidin (SAV-DNAse) that renders the conjugate capable of binding to the modified nucleotide but not to the nucleic acid that does not contain the modified nucleotide. The reagents include a modified deoxynucleoside triphosphate for incorporation as a modified nucleotide into copies of the nucleic acid during the amplification (NTP-B). If the modified deoxynucleoside triphosphate is present initially in the combination, as shown in FIG. 1, it should be protected as mentioned above by incorporation into a wax pellet or the like. If not protected, the modified deoxynucleoside triphosphate should be added after the initial incubation period during which the conjugate binds to any modified nucleotides in the contaminant, which is then rendered unamplifiable by the enzyme of the conjugate. In the example in FIG. 1 PCR is conducted to amplify TPN. Accordingly, PCR primers P1 and P2 are included in the reaction mixture.

In this embodiment of the invention, the combination is first subjected to conditions wherein the receptor binds to the modified nucleotide in the copies, if present, and the nuclease degrades the copies without degrading the nucleic acid. In FIG. 1 sample 1 is not contaminated with copies containing the modified nucleotide. Following the above incubation, the combination is subjected to conditions wherein the enzyme conjugate is no longer active, the wax pellet melts releasing the NTP-B, and the nucleic acid is amplified. In PCR the thermal cycling accomplishes all of the above. The copies of TPN produced during the amplification, referred to as MTPN, contain one or more modified nucleotides and are detected at the conclusion of the amplification.

As can be seen in FIG. 1, the amplification of additional samples beginning with sample 2 containing target nucleic acid TPN, is conducted in the same manner. To this end, the sample is combined with the NTP's and the wax-encapsulated NTP-B, SAV-DNAse, and PCR primers P1 and P2. This combination may also contain MTPN as a contaminant. In the initial incubation the SAV-DNAse conjugate binds to the biotinylated nucleic acid in the contaminant by virtue of the streptavidin binding to the biotin on the MTPN. The DNAse degrades the MTPN to give DMTPN's, which are not amplifiable during the amplification. As can be seen from FIG. 1, the copies of TPN, namely, MTPN, produced in this part of the reaction scheme all contain at least one biotinylated nucleotide. After the thermal cycling is discontinued, the amplified product MTP2 is detected.

It is within the purview of the present invention to introduce a modified nucleotide into the copies of the nucleic acid by employing, either in conjunction with a modified nucleoside triphosphate or in place thereof, an oligonucleotide primer that is modified, that is, contains one or more modified nucleotides. Extension of this primer during the amplification yields a copy of the nucleic acid that contains a modified nucleotide.

The following description sets forth such appropriate conditions for carrying out the contaminant removal and the amplification in accordance with the present invention, which are subject to modification by those skilled in the art depending on the specific reagents and other molecules chosen for any particular application.

Generally, an aqueous medium is employed. Other polar cosolvents may also be employed in the medium, usually oxygenated organic solvents of from 1–6, more usually from 1–4, carbon atoms, including alcohols, ethers and the like. Usually, these cosolvents are present in less than about 70 weight percent, more usually, in less than about 30 weight percent.

It is important in the present invention that the nuclease be sufficiently deactivated so that it preferentially degrades the polynucleotide to which the enzyme conjugate is bound by virtue of the binding of the sbp member of the conjugate and the sbp member of the polynucleotide or that conditions be chosen so that such a situation can be achieved or a combination of both. In many cases the conjugation of the nuclease to the sbp member provides for a sufficient deactivation of the nuclease. Reducing the activity of the enzyme has a large effect on the ability of the enzyme to degrade a polynucleotide other than that to which the enzyme conjugate is bound, but only a small effect on its ability to degrade the polynucleotide to which the conjugate is bound. Usually, the enzyme is deactivated to a level of about 50 to 99.9%, preferably, 90 to 99%. The deactivation of the enzyme is dependent on a number of factors including the particular enzyme, such as temperature, pH, ionic strength, presence of inhibitors such as specific inhibitors and antibodies to the enzyme, and so forth. Generally, relatively small amounts of the enzyme conjugate are employed in keeping with the underlying concern, which is the contamination of a subsequent amplification by one or more molecules of polynucleotide contaminant from a previous reaction. The amount of enzyme conjugate employed is usually about 10 picomolar to 10 micromolar, preferably, 1 nanomolar to 1 micromolar. It will be appreciated that the amount of enzyme conjugate can vary depending on the level of deactivation of the enzyme and/or the conditions employed for the reaction and/or the expected level of contamination. For this part of the reaction scheme the pH can be chosen to minimize the activity of the enzyme in the enzyme conjugate so that only polynucleotide to which the enzyme conjugate is bound is degraded and not other polynucleotides that are present in the reaction mixture. For this purpose the pH may be high, being about 6 to 10 preferably, about 7 to 9. The temperature can also be chosen to optimize the binding of the sbp member to its complementary member and to minimize the activity of the enzyme in the enzyme conjugate so that only polynucleotide to which the enzyme conjugate is bound is degraded and not other polynucleotides that are present in the reaction mixture. Accordingly, the temperature at which this part of the reaction scheme is conducted is about 5° to 60° C., preferably, about 15° to 50° C. It is, of course, within the scope of the present invention to use lower pH or higher temperature for this part of the reaction scheme if the enzyme in the enzyme conjugate is sufficiently deactivated so that only polynucleotide to which the enzyme conjugate is bound is degraded. The degradation is conducted for a time sufficient to achieve, in accordance with the present method, destruction of any contaminant present in the reaction mixture without destroying the nucleic acid of interest, namely, the polynucleotide analyte. Generally, the time period for this part of the reaction is from about 1 to 60 minutes, preferably, about 5 to 10 minutes. In the example shown in FIG. 1 the reaction mixture is held at 25° C. for 10 minutes.

Following the above part of the reaction scheme the reaction mixture is treated to render the enzyme conjugate incapable of degrading nucleic acid. This may be accomplished preferably and most conveniently by heating the reaction mixture to a level to destroy the catalytic activity of the enzyme. In this regard the reaction mixture is heated to a temperature less than 99° C., preferably, about 50° to 99° C. Other ways to achieve this end will be suggested to those skilled in the art and are discussed above.

The pH of the medium for the remaining part of the reaction scheme that includes the amplification is usually in the range of about 5.5 to 10, more usually, in the range of about 6.5 to 9.5, and, preferably, in the range of about 7 to 9. The pH and temperature are chosen and varied, as the case may be, so as to cause, either simultaneously or wholly or partially sequentially, dissociation of any internally hybridized sequences, hybridization of a primer with single stranded polynucleotides and extended primer once primer has been extended, extension of primer along single stranded polynucleotides and extended primer, and dissociation of the extended primer from its duplex. In some instances, a compromise will be made in optimizing the speed, efficiency, and specificity of these steps depending on whether it is desired to perform the above steps wholly or partially sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the amplification. The temperatures employed are dependent on a number of considerations such as, for example, the salt concentration and the pH of the medium, the solvent composition of the medium used, the length of the polynucleotide analyte and the length and nucleotide composition of the primer(s).

Normally, in conducting the amplification of nucleic acids, the medium is cycled between two or three temperatures (thermal cycling). The temperatures for the present method in conjunction with amplification generally range from about 10° to 105° C., more usually from about 40° to 99° C., preferably 50° to 98° C. Relatively low temperatures of from about 40° to 80° C. can be employed for the hybridization steps, while denaturation and extension can be carried out at a temperature of from about 80° to 105° C. The amplification is conducted for a time sufficient to achieve a desired number of copies for an accurate assay for a polynucleotide analyte. Generally, the time period for conducting the method is from about 10 seconds to 10 minutes per cycle and any number of cycles can be used from 1 to as high as 100 or more, usually 5 to 80, frequently 10–60. As a matter of convenience it is usually desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer. Generally, the time period for conducting the amplification method is from about 5 to 200 minutes.

In the application of the present invention to LCR, one utilizes at least one oligonucleotide capable of binding to a polynucleotide analyte. The oligonucleotide contains at least one, and preferably three or more, modified nucleotides in accordance with the present invention. The modified nucleotide may be present in the oligonucleotide at any position other than an end that is contiguous with the end of another oligonucleotide used in LCR. Procedures for preparing oligonucleotides are known in the art and are discussed above. Such procedures can be easily adjusted for the preparation of oligonucleotides having one or more modified nucleotides as mentioned above.

Amplified nucleic acid can be detected in numerous ways. For example, molecules of the polynucleotide primer can be labeled with a reporter molecule such as a ligand, a small organic molecule including fluorescers, chemiluminescers, photosensitizers and the like, catalysts, co-enzymes, radioactive substances, amplifiable polynucleotide sequences, a polypeptide, a support, an operator or the like. Examples of particular labels or reporter molecules and their detection can be found in U.S. patent application Ser. No. 07/555,323 filed Jul. 19, 1990, the relevant disclosure of which is incorporated herein by reference. Other assay formats and detection formats are disclosed in U.S. patent application Ser. Nos. 07/229,282, abandoned and 07/399,795, abandoned filed Jan. 19, 1989, and Aug. 29, 1989, respectively, U.S. patent application Ser. No. 07/555,323 filed Jul. 19, 1990, U.S. patent application Ser. No. 07/555,968, U.S. Pat. No. 5,439,793 filed Jul. 19, 1990, U.S. patent application Ser. No. 07/776,538 filed Oct. 11, 1991, abandoned, U.S. patent application Ser. No. 07/923,079 filed Jul. 31, 1992, abandoned, all of which have been incorporated herein by reference. Any standard method for specifically detecting nucleic acid sequences can be used.

One particular method for detecting amplified nucleic acid is described in U.S. patent application Ser. No. 07/704, 569 filed May 22, 1991 (Ullman, et al.), the relevant disclosure of which is incorporated herein by reference. The method comprises treating the reaction mixture suspected of containing the amplified nucleic acid analyte under conditions such that the analyte, if present, causes a photosensitizer and a chemiluminescent compound to come into close proximity. The photosensitizer generates singlet oxygen and activates the chemiluminescent compound when it is in close proximity. The activated chemiluminescent compound subsequently produces light. The amount of light produced is related to the amount of analyte in the medium.

In a specific example in accordance with the present invention DNase I is conjugated to antibodies to Br-UTP to give conjugate A. In this example of the present method a PCR amplification is carried out wherein a medium containing DNA from *N. Gonorrhoea* (the "target DNA") is combined with dATP, dGTP, dCTP and dTTP, two PCR primers comprised of 24 base oligonucleotides that hybridize to sites on the target DNA that are separated by 700 bases, conjugate A and Taq polymerase. The mixture is incubated for 1 hour at 30° C., and Br-UTP is added and the medium is cycled 45 times between 65° and 95° C. for 3 minutes at each temperature. The product of this amplification (the "modified target DNA") appears as a 748 base pair band on gel electrophoresis after staining with ethidium bromide. When a small portion of this modified target is added in place of the above medium to a PCR amplification carried out in the same way, no band corresponding to 748 bases is obtained upon electrophoresis. No copies of the modified target DNA are detected.

In an assay for t-RNA from *M. tuberculosis* in accordance with the present invention, a mixture is formed that includes the sample suspected of containing the above t-RNA, a 20-mer DNA primer, reverse transcriptase, nucleoside triphosphates and a conjugate of DNase I and streptavidin (the "conjugate"). After the mixture is incubated at 40° C. for 30 minutes, the mixture is heated to 100° C. for 5 minutes and Pfu polymerase, biotinylated dUTP and a second DNA primer identical to a 20 nucleotide sequence in the t-RNA, which sequence is 400 nucleotides 5' of the first DNA primer binding site, are added. The mixture is repeatedly cycled from 60° C. to 75° C. to 95° C. After 45 cycles the 440 nucleotide amplification product is separated by gel electrophoresis and transferred to a nitrocellulose membrane (Southern blot). A digoxin-oligonucleotide conjugate, having 24 nucleotides, in Tris buffer, pH 8.0 is incubated with horseradish peroxidase-antidigoxin conjugate. After washing, the membrane is incubated with 2,5,2',5'-tetramethylbenzidine and hydrogen peroxide. The appearance of a blue color indicates the presence of t-RNA from *M. tuberculosis* in the sample. If a small portion of the band in the gel containing the amplified product is introduced into a second assay that did not contain t-RNA from *M. tuberculosis,* no blue color is observed.

In an assay for chlamydia in accordance with the presence invention, a mixture is formed by combining the sample suspected of containing chlamydia antigen, a thermally stable ligase, a double-stranded biotin-labeled 24 nucleotide probe complementary to the chlamydia target DNA and a conjugate of DNAse I and antibody to 2-aminofluorene. After incubation of the mixture for 30 minutes at 40° C., the mixture is heated to 100° C. for 10 minutes and cooled to room temperature, and 2-aminofluorene-labeled 24-nucleotide double stranded oligonucleotide is added that can bind to a site contiguous with the site on the target DNA to which the first probe binds. ATP is added and the temperature is cycled between 70° C. and 95° C. for 45 cycles and the mixture is allowed to stand in a microtiter well coated with streptavidin. The well is washed, HRP-labeled antibodies to aminofluorene are added, and the well is washed again. ABTS and hydrogen peroxide are added and the color that develops after 30 minutes indicates the presence of the target DNA. If a very small portion of the solution to be added to the microtiter well is introduced into a second assay, no color is produced even when color is produced in the first assay.

As a matter of convenience, reagents for conducting the present method can be provided in packaged combination in a kit in predetermined amounts. The kits can be used in accordance with the methods of the present invention in determining a polynucleotide analyte. In one embodiment the kit comprises in packaged combination: (a) nucleoside triphosphates, for example, those selected from the group consisting of dATP, dCTP, dGTP and dTTP, wherein one of the nucleoside triphosphates is modified, (b) a polynucleotide polymerase such as DNA polymerase, (c) at least one oligonucleotide such as a polynucleotide primer, and (d) a conjugate comprising a nuclease, such as a DNAse, and a receptor that binds to an amplified nucleic acid produced from the modified deoxynucleoside triphosphate wherein the receptor does not bind to the nucleic acid. The kit can further comprise a description of a method for conducting a degradation of a contaminant and an amplification of a nucleic acid utilizing the kit. Such description can be found, for example, in a package insert included in the kit. The kit can also comprise a labeled probe that binds to the nucleic acid.

Another embodiment of the present invention is a kit for amplifying a nucleic acid comprising in packaged combination a conjugate of a receptor and a nuclease, an oligonucleotide, and nucleoside triphosphates, wherein at least one of either the nucleoside triphosphates or the oligonucleotide is modified and wherein the receptor binds to amplified nucleic acid produced from the modified nucleoside triphosphates and the oligonucleotide and not to the nucleic acid.

The kit can further include a labeled or unlabeled polynucleotide probe capable of binding to extended primer produced in an amplification. The kit can further include members of a signal producing system and also various buffered media, some of which may contain one or more of the above reagents.

The relative amounts of the various reagents in the kits can be varied widely to provide for concentrations of the reagents that substantially optimize the reactions that need to occur during the present method and to further substantially optimize the sensitivity of any assay, in which the present method is employed. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit.

EXAMPLES

The invention is further demonstrated by the following illustrative examples, which should not be construed as a limitation on the scope of the present invention. Parts and percentages are by weight unless otherwise indicated. Temperatures are in degrees Centigrade unless indicated otherwise.

The following abbreviations are used herein:

NHS—N-hydroxy succinimide

NHS-LC-biotin—sulfosuccinimidyl-6-(biotinamido)hexanoate

KD—kilodalton

Tris—hydroxymethylaminomethane

DTT—dithiothreitol

EDTA—ethylenediaminetetraacetate

SDS—sodium dodecylsulfate

CTAB—cetyltrimethylammonium bromide

TE—Tris-EDTA

EDAC—ethyl-dimethylaminio-propyl-carbodiimide

CBD—carboxybenzyldextran

MES—2-(N-morpholino)ethanesulfonic acid

HPLC—high performance liquid chromatography

KRPM—one thousand rounds per minute

HABA—4'-hydroxyazobenzene-2-carboxylic acid

Example 1

1. Preparation of DNaseI—Streptavidin conjugate

Deoxyribonuclease I (Pharmacia, Piscataway, N.J. (Pharmacia)) was dialyzed against sodium phosphate buffer to remove excess amine. NHS-LC-biotin (Pierce Chemical Company, Rockford, Ill., (Pierce) catalogue no. 21335) was then added to form a DNaseI-biotin conjugate. Dialysis against sodium phosphate buffer was again performed to remove excess biotin. At the end of dialysis, Streptavidin (Aaston, Wellesley, Mass. (Aaston)) was introduced to the mixture, and a DNaseI-Streptavidin conjugate was produced. The conjugate was further purified by an ultra gel—44 sizing column (Ultrogel ACA 44, Sepracor, Malbourough, Mass., catalogue no. ACA44230161). The details are given below.

Six bottles of lyophilized Deoxyribonuclease I (Pharmacia, #27-0512) were resuspended in 2 ml of 50 mM sodium phosphate buffer at pH 8.0 (buffer A). Since the lyophilized DNase I contains 20% glycine, dialysis against buffer A (with three times 1 liter buffer change) was performed to eliminate the amine. At the end of dialysis, the DNase I concentration was measured by O.D. 280 and 17.6 mg of protein was recovered. At the same time, 10 mg of NHS-LC-biotin (Pierce, #21335) was resuspended in 100 µl of water and 316 µl of this solution was added to above dialyzed DNase I (the molar ratio of NHS-LC-biotin to DNase I was 20 to 1). This mixture was stirred at room temperature for 10 minutes and kept overnight at 4° C. On the following day, dialysis was performed on the biotin-DNase I mixture against 50 mM Tris-Cl buffer at pH 7.4 (buffer B) in order to remove unbound biotin. The number of biotins per DNase I molecule was then measured by HABA assay (Savage, "Avidin-Biotin Chemistry: A Handbook," Pierce) and was determined to be about three biotin molecules per DNase I molecule.

One bottle of lyophilized streptavidin (Aaston, #1STA1191) was dissolved in 20 ml of buffer B and was subsequently dialyzed against buffer B (with three times 1 liter buffer exchange) to remove inert ingredients (mainly lactose and NaCl). DNase I-Streptavidin conjugate was made by adding above biotin-DNase I (23 mg in the volume of 2.5 ml) drop by drop to dialyzed streptavidin (1.1 g in the volume of 25 ml). The reaction mixture was then stirred at room temperature for 1.5 hours and stored at 4° C.

The DNase I-streptavidin conjugate purification was carried out in a cold room by using an Ultragel AcA44 column (Sepracor) with buffer C (50 mM Tris-Cl, pH 7.4 and 170 mM NaCl). The size of the column was 550 ml (2.5 cm diameter wide×110 cm height). After pre-washing the column with two column volumes of buffer C, 4 ml of un-purified conjugate mixture (at a concentration of 10 mg/ml) was loaded on to the column and the column was run at a flow rate of 32 ml/hour. About 200-4.2 ml fractions were collected and all fractions were subjected to a BCA (Bicinchoninic Acid) protein assay (according to the manufacturer's catalog and handbook, Pierce). The first peak, which represented DNase I-Streptavidin conjugate, appeared at fraction #50 and ended at fraction #59. The second peak, which represented excess streptavidin, appeared at fraction #77 and ended at fraction #99. Fractions #50 to #59 were pooled together and concentrated by a Centriprep-30 concentrator (Amicon). An 8% Tris-Glycine SDS gel was then performed to confirm the purification.

The size of the conjugate was about 210 KD and there were three Streptavidin molecules attached for every DNase I molecule. Overall, there were nine biotin binding sites per conjugate.

2. *Mycobacterium tuberculosis* DNA

Cells (*Mycobacterium tuberculosis* (M.tb)) were grown in Middlebrook 7H9 broth at 37° C. and then the cells were transferred into microfuge tubes and heated at 80° C. for 20 minutes. The cells were spun down for 3 minutes and the supernatant was discarded. The resulting pellet was resuspended in 500 microliters of 10 mM Tris, 1 mM EDTA at pH 8.0. Then, 50 microliters of 10 mg/ml freshly prepared lysozyme was added and the mixture was incubated at 37° C. for 1 hour. Next, 70 microliters of 10% SDS was added and 6 microliters of 10 mg/ml Proteinase K (frozen aliquots) was added. This mixture was incubated a 65° C. for 10 minutes and then 100 microliters of 5M NaCl was added. Following this step 80 microliters of 10% CTAB/4% NaCl was added and the mixture was incubated at 65° C. for 10 minutes. An equal volume (to that of the reaction mixture) of chloroform/isoamyl alcohol (24/1 v/v) was added and the contents were mixed well before being centrifuged for 5 minutes. The supernatant was removed to a clean tube and 0.6 volume of isopropanol was added to precipitate the DNA. The sample was kept a −20° C. for 30 minutes to complete precipitation and then the mixture was centrifuged for 20 minutes. The pellet was washed 1× with cold (0° C.) 70% aqueous ethanol and the mixture was centrifuged for 5 minutes at room temperature. The DNA pellet was dried briefly and resuspended in 10–20 microliters of TE buffer. Concentrations of genomes were calculated from an $A_{260}$ of total DNA and serial dilution of the stock. The genome size of M.tb is $2.5 \times 10^9$ Daltons, which corresponds to about $3.8 \times 10^6$ base pairs.

3. Preparation of Primer and Blocker Oligonucleotides

A primer oligonucleotide (Primer 1) and a blocker oligonucleotide (Blocker 1) were designed to amplify the IS6110 region of M.tb. The primer and the blocker had the following sequences respectively:

Primer 1  5' ACTGGTAGAGGCGGCGATGGTTGAA 3' (SEQ ID NO:1)

Blocker 1  5' ACTGGTAGAGGCGGCGATGGTTGAATAACCCTGAA

TTCAGGGTTAGCCACACTTTGCGGGCACCGTAAAC 3'

(SEQ ID NO:2)

The expected amplification product was one having 638 base pairs.

Another primer oligonucleotide (Primer 2) and blocker oligonucleotide (Blocker 2) were designed to amplify a 65-KD antigen gene of M.tb. The primer and the blocker had the following sequences respectively:

Primer 2  5' TAGCCCTTGTCGAACCGCATACCCT 3' (SEQ ID NO:3)

Blocker 2  5' TAGCCCTTGTCGAAGCGCATACCCTGTGTGTCCATA

TGGACACACCATCGTTGGTGATCGTGGGGGCACC 3'

(SEQ ID NO:4)

The expected amplification product was one having 450 base pairs.

The above primer and blocker oligonucleotides were synthesized on a Pharmacia Gene Assembler DNA synthesizer (Pharmacia) through standard phosphoramidite methodology. Blockers were purified by HPLC (Shimadzu, Kyoto, Japan). Primers were purified by standard butanol extraction.

4. Preparation of biotinylated amplicon

A 450 base pair (bp) biotinylated amplicon was generated by performing an amplification of M.tb with Primer 2, Blocker 2, and biotin-dUTP (Boehringer Mannheim, Indianapolis, Ind.). The amplification composition was 1 µM Primer 2, 50 nM Blocker 2, 10 mM Tris-Cl (pH8.8), 50 mM KCl, 1.5 mM $MgCl_2$, 0.1% Triton X-100, 7.5 mM DTT, five units cloned Pfu polymerase (Strategene, La Jolla, Calif.), 200 µM dATP, 200 µM dGTP, 200 µM dCTP, 180 µM dTTP and 20 µM biotin-dUTP (the molar ratio of dTTP:biotin-dUTP=9:1). With the presence of $10^4$ M.tb genomic DNA targets, the amplification was carried out on an Ericomp thermal cycler (Ericomp, San Diego, Calif.) for 45 cycles. The amplification mixture was cycled at the following temperatures: 95° C. for 4 minutes for denaturation followed by 45 cycles of 94° C. for 1 minute, 66° C. for 1 minute and 72° C. for 1 minute. After the temperature cycling was completed, the biotinylated amplicon (450 bp) was purified by agarose gel electrophoresis.

5. Prevention of amplification of biotinylated amplicon

DNaseI-Streptavidin conjugate (the "Conjugate") in the amount of $1.8 \times 10^{12}$ molecules was mixed with the number of molecules of biotinylated amplicon (produced as described above) indicated below for each respective reaction mixture. Each reaction mixture (20 µl) was then incubated at 37° C. for 10 minutes. At the end of the incubation, amplification of each reaction mixture was conducted by adding 80 µl of the amplification composition, described in paragraph 4 above, to each of the 20 µl reaction mixtures from above and cycling 45 cycles in an Ericomp thermal cycler at the temperatures set forth above in paragraph 4.

FIG. 2 shows the results for amplification of each reaction mixture either with or without the Conjugate. In FIG. 2 Lanes 1–7 are the reaction mixtures containing the Conjugate and having $10^5$, $10^4$, $10^3$, $10^2$, 10, 1 and 0 molecules of biotinylated amplicon, respectively. Lanes 8–14 are the reaction mixtures containing no Conjugate and having $10^5$, $10^4$, $10^3$, $10^2$, 10, 1 and 0 molecules of biotinylated amplicon, respectively. Lane M is DNA 123 bp marker. The arrows indicate the 450 bp line.

The results of this experiment demonstrated that the DNaseI-Streptavidin conjugate used as described above achieved prevention of amplification of up to $10^4$ biotinylated amplicons as a contaminant in the above reaction mixtures.

6. One-step amplification of genomic target with prevention of contaminant amplification A 100 µl reaction mixture (Mixture 1) was prepared containing $10^4$ biotinylated amplicons, prepared as in paragraph 3 above, and $1.8 \times 10^{12}$ molecules of the Conjugate. Also in Mixture 1 were $10^3$ molecules of M.tb genomic target DNA, 10 mM Tris-Cl (pH8.8), 50 mM KCl, 1.5 mM $MgCl_2$, 0.1% Triton X-100, 7.5 mM DTT, five units cloned Pfu polymerase (Stratagene), 200 µM dATP, 200 µM dGTP, 200 µM dCTP, 180 µM dTTP.

Mixture 1 was incubated at 37° C. for 10 minutes and then Primer 2 for biotinylated amplicon amplification was added (0.5 µl of a stock solution (100 µM) of Primer 2 was added to 50 µl of reaction mixture to give a final concentration of 1 µM). Mixture 1 was placed directly into an Ericomp cycler for amplification under the cycling conditions described above in paragraph 4 of this Example 1 in order to monitor biotinylated amplicon amplification.

Additional experiments were carried out similarly to that described above using Mixture 2, Mixture 3, Mixture 4 or Mixture 5, respectively, in place of Mixture 1:

a) Mixture 2 did not contain the Conjugate. After incubation of Mixture 2 as described above, Primer 1 (0.5 µl of a stock solution (100 µM) of Primer 1 was added to 50 µl of reaction mixture to give a final concentration of 1 µM) and Blocker 1 (0.5 µl of a stock solution (5 µM) of Blocker 1 was added to 50 µl of reaction mixture to give a final concentration of 50 nM) were added to the reaction mixture (Mixture 2, Part 1), which was then placed directly into an Ericomp cycler for amplification under the cycling conditions described above in paragraph 4 of this Example 1 in order to monitor genomic DNA target amplification. Primer 2 (final concentration of 1 µM) for biotinylated amplicon amplification was added to the other half (50 µl) of Mixture 2 (Mixture 2, Part 2). Amplification was then performed in an Ericomp cycler at the cycling conditions described in paragraph 4 above.

b) Mixture 3 was subjected to the same procedure as that described above for Mixture 2. Mixture 3 was the same as Mixture 1 except for 10 molecules (in place of $10^2$ molecules) of M.tb genomic target DNA; the 50 µl aliquots of the reaction mixture, treated as described above in part a), are referred to below as Mixture 3, Part 1, and Mixture 3, Part 2, respectively.

c) Mixture 4 was subjected to the same procedure as that described above for Mixture 2. Mixture 4 was the same as Mixture 1 except for $10^2$ molecules (in place of $10^3$ molecules) of M.tb genomic target DNA; the 50 µl aliquots of the reaction mixture, treated as described above in part a), are referred to below as Mixture 4, Part 1, and Mixture 4, Part 2, respectively.

d) Mixture 5 was subjected to the same procedure as that described above for Mixture 2. Mixture 5 was the same as Mixture 1 (and therefore contained $10^3$ molecules of M.tb genomic target DNA); the 50 µl aliquots of the reaction mixture, treated as described above in part a) of this paragraph 6 of this Example 1, are referred to below as Mixture 5, Part 1, and Mixture 5, Part 2, respectively.

The results are shown in FIG. 3 with the lanes defined as follows:

Lane 1 is Mixture 1 as a positive control.
Lane 2 is Mixture 2, Part 2.
Lane 3 is Mixture 2, Part 1.
Lane 4 is Mixture 3, Part 2.
Lane 5 is Mixture 4, Part 2.
Lane 6 is Mixture 5, Part 2.
Lane 7 is Mixture 3, Part 1.
Lane 8 is Mixture 4, Part 1.
Lane 9 is Mixture 5, Part 1.
Lane M is DNA 123 bp marker.

The results demonstrated that the DNaseI-Streptavidin conjugate was able to selectively digest biotinylated amplicon contaminant, not genomic target DNA. In addition, the results demonstrated that prevention of contaminant amplification and genomic target amplification were carried out in the same reaction vessel as part of a single procedure.

Example 2

1. Preparation of CBD

To five grams of dextran (Pharmacia, $2 \times 10^6$ daltons) dissolved in 80 ml deionized water was added 6 g of chloromethylbenzoic acid, 7 g of sodium hydroxide, 5 g of potassium iodide, 50 mg EDTA and 50 mg of sodium borohydride. The mixture was warmed to 60° C. in an oil bath when it turned to a clear solution, which was stirred at 60° C. for one hour. After being cooled, the solution was added dropwise to 400 ml ethanol. A white solid was collected and was redissolved in water. The solution was added dropwise to 400 ml ethanol and the white powder obtained was dried in vacuum. $^1$H NMR (CD3OD): 3.1–3.9, 4.5–4.9, 7.2–7.5.

2. Preparation of DNaseI—Streptavidin conjugate beads

Carboxypolystyrene beads (175 nM) from Bangs Laboratories, Inc., Carmel, Ind. (Bangs)) were reacted with 2,2'-oxybis(ethylamine) dihydrochloride (Aldrich Chemical Co., Milwaukee, Wis. (Aldrich)) and EDAC (Sigma Chemical Co., St. Louis, Mo. (Sigma)). Next, the beads were reacted with CBD from above to give dextran coated beads, which were then reacted with EDAC and NHS ester, followed by reaction with DNase I and streptavidin. The details of this procedure are given below.

To a suspension of 50 mg carboxypolystyrene beads in 20 ml MES buffer (0.1M, pH 6) (MES purchased from Research Organics, Inc., Cleveland, Ohio) were added 195 mg of oxybis (ethylamine) dihydrochloride and 100 mg EDAC in 5 ml the same MES buffer. The mixture was stirred at room temperature for two hours. After centrifugation (15 KRPM, 30 minutes) the beads were washed three times with 10 ml sodium borate buffer (0.2M, pH 9) and suspended in the MES buffer.

Quantitation of amino groups on the bead surface was carried out as follows: To 150 µl ninhydrin reagent (Sigma) was added 50 µl deionized water containing either a given amount of ethanolamine (as a reference) or 1 mg amine-modified beads (from above). The mixture was then heated in a 100° C. heat block for 10 minutes. After cooling, 1 ml 50% ethanol in water was added to the solution (suspension). The beads were removed by centrifugation (15 KRPM, 15 minutes), and the absorbance of the supernatant at 574 nm was determined.

300 mg CBD dextran (prepared as described above) was dissolved in 22 ml of buffer D (0.1M MES, pH6, 0.3M NaCl) and mixed for 15 minutes at room temperature. To this dextran was added 100 mg N-hydroxysuccinimide (Aldrich) and 100 mg of EDAC (Sigma) (both were previously dissolved in 1 ml of buffer D). After stirring the reaction at room temperature for 30 minutes, solution of a 1 ml amine-modified beads (from above) at the concentration of 50 mg/ml was added slowly and this reaction was stirred at room temperature overnight.

In order to remove excess dextran, several washing steps were performed: beads were pelleted with centrifugation and resuspended in buffer E (0.1M MES, pH6) with brief sonication. After washing two more times, beads were then heated at 95° C. for 10 minutes. One more washing was performed following this heating step.

The amount of dextran in the bead preparation was measured by an Anthrone test (modification of procedure described by Jermyn, *Analytical Biochemistry* (1975) 68:332). To a sample (1 ml) in a 25 ml test tube (13×100 mm) are added concentrated hydrochloric acid (1 ml) and 90% formic acid (0.1ml) followed by freshly prepared anthrone reagent (8ml), slowly enough to avoid excessive bubbling. The anthrone reagent was prepared by dissolving anthrone (Aldrich Chemical Company, Milwaukee, Wis.) (20 mg/100 ml) in 80% (v/v) sulphuric acid at room temperature. After thorough mixing of its contents, the tube, together with others containing appropriate standards and blanks, was heated (12 min.) in a boiling water bath and immediately plunged into a cold water bath. Optical density was read at 630 nm after stirring on a Vortex mixer and allowing to stand 5 min. to disperse bubbles. It was determined that there was about 3% dextran in this bead preparation.

Streptavidin (Aaston) and DNase I (Pharmacia) were both dialyzed against buffer F (10 mM MES, pH6). A 20 mg/ml sulfo-NHS solution was made by dissolving 10 mg of sulfo-NHS (Pierce) in 500 µl buffer F and a 10 mg/ml EDAC solution was also made by dissolving 5 mg of EDAC (Sigma) in 500 µl buffer F. From these reagents, four mixtures were made as follows: 5 mg streptavidin plus 2 mg sulfo-NHS and 1 mg EDAC (preparation #1); 2.5 mg streptavidin and 2.5 mg DNase I plus 2 mg sulfo-NHS and 1 mg EDAC (preparation #2); 5 mg streptavidin and 0.5 mg DNase I plus 2 mg sulfo-NHS and 1 mg EDAC (preparation #3); 0.5 mg streptavidin and 5 mg DNase I plus 2 mg sulfo-NHS and 1 mg EDAC (preparation #4). Preparation #1 was added slowly to 10 mg of CBD dextran coated beads, and the reaction mixture was stirred at room temperature for 5 hours. The same procedure was applied to preparation #2, preparation #3 and preparation #4, respectively. Thus, four bead preparations were made and each of them had different amounts of streptavidin and DNase I.

Streptavidin and DNase I coated beads were washed in buffer G (0.1M Tris-Cl, pH8, and 0.1% BSA) and then 1× buffer (10 mM Tris-Cl, pH8.8, 50 mM KCl, 1.5 mM MgCl$_2$, 0.1% Triton X-100, 7.5 MM DTT). The washing procedure was the same as above.

To analyze these beads, we used a $^3$H-biotin binding assay to study the amount of streptavidin on the beads. In this assay 100 µl of 0.5–8 µg of sonicated beads were added to microfuge tubes followed by 500 µl of 8.99 pmoles (1:1250 of 1 Ci/µl) of $^3$H-biotin in assay buffer (0.1M Tris, 0.3M NaCl, 25 mM EDTA, 1/320 HBR-1 (Heterophilic Blocking Reagent, Scantibodies, Inc., Santee, Calif.), 0.05% Kathon (Rohm and Haas, Philadelphia, Pa.), 1 mg/ml BSA, 1 mg/ml Dextran T-500 (Pharmacia), pH 8.2). The mixture was incubated for 1 hour a room temperature and then was centrifuged in a microfuge for 45 minutes at 14000 rpm. Supernatants (60 µl) of the reaction mixture in 10 ml of Ready Safe scintillation cocktail (Beckman Instruments, Inc., Fullerton Calif.) were counted. The moles of biotin bound per test were calculated and the specific activity was determined from the total counts. The number of streptavidin molecules per bead was calculated, assuming 4 biotins per one streptavidin and knowing 1.9×10$^8$ 212 nm beads per µg. The BCA protein assay was used to study the total amount of protein on the beads. The difference from these two assays was the amount of DNase I on the beads. Based on this calculation method, about 3670 streptavidin molecules per bead for beads preparation #1, 1900 streptavidin molecules and 1250 DNase I molecules per bead for beads preparation #2, 2400 streptavidin molecules and 1300 DNase I molecules per bead for beads preparation #3, 650 streptavidin and 2330 DNase I per bead for beads preparation #4. Beads of preparation #2 were used herein in amplifications conducted in accordance with the present invention. The bead preparation contained 3.4×10$^{14}$ beads/gram and each 10 µl of the bead preparation had 10 µg of beads.

3. Prevention of amplification of biotinylated amplicon

The procedure described above for Example 1, part 5, was followed except that 10 µl of the DNase I-streptavidin conjugate bead preparation from above was used in place of 10 µl of the DNase I-streptavidin conjugate used in Example 1, part 5, and except that, besides biotinylated amplicon, Mycobacterial Bovis BCG genomic DNA (BCG genomic DNA), which was prepared by a procedure identical to that used in Example 1, part 2 (except that Mycobacterial Bovis cells were employed in place of M.tb cells) was used as a control target molecule in separate, additional reactions. The size of the BCG genomic DNA is the same as M.tb genomic target DNA. For the IS6110 region there are one or two copies per genome in the case of BCG genomic DNA whereas, in the case of M.tb genomic target DNA, there are about 10 per genome. For the 65 KD heat shock protein region, both BCG genomic DNA and M.tb genomic target DNA have only one copy per genome.

The results are summarized in FIGS. 4 and 5. FIG. 4 represents a control experiment in that no beads were present in any of the reaction mixtures.

In FIG. 4 Lanes 1–8 are reaction mixtures containing no beads and having 0, 1, 10, $10^2$, $10^3$, $10^4$, $10^5$ and $10^6$ molecules of biotinylated amplicon, respectively. Lanes 10–16 are reaction mixtures containing no beads and having 1, 10, $10^2$, $10^3$, $10^4$, $10^5$ and $10^6$ molecules of biotinylated amplicon, respectively. Lanes 9 and 17 are DNA 123 bp marker. The arrows indicate the 450 bp line. Lane 18 is a negative control, namely, a reaction mixture that had $10^6$ molecules of BCG genomic DNA and Primer 1 only (no Blocker 1 was added).

In FIG. 5 Lanes 1–8 are reaction mixtures containing 10 μg beads per reaction mixture and having 0, 1, 10, $10^2$, $10^3$, $10^4$, $10^5$ and $10^6$ molecules of biotinylated amplicon, respectively. Lanes 10–16 are reaction mixtures containing 10 μg beads per reaction mixture and having 10, $10^2$, $10^3$, $10^4$, $10^5$ and $10^6$ molecules of biotinylated amplicon, respectively. Lanes 9 and 16 are DNA 123 bp marker. The arrows indicate the 450 bp line. Lane 17 is a negative control, namely, a reaction mixture that had $10^6$ molecules of BCG genomic DNA and Primer 1 only (no Blocker 1 was added).

The results demonstrated that the DNaseI-Streptavidin conjugate bead reagent was able to selectively digest biotinylated amplicon contaminant, not genomic target DNA. Under the same reaction conditions wild-type target, namely, BCG genomic DNA, was not digested by the bead reagent. In addition, the results demonstrated that prevention of contaminant amplification and genomic target amplification was carried out in the same reaction vessel as part of a single procedure.

The above discussion includes certain theories as to mechanisms involved in the present invention. These theories should not be construed to limit the present invention in any way, since it has been demonstrated that the present invention achieves the results described.

The above description and examples disclose the invention including certain preferred embodiments thereof. Modifications of the methods described that are obvious to those of ordinary skill in the art such as molecular biology and related sciences are intended to be within the scope of the following claims and included within the metes and bounds of the invention.

---

What is claimed is:

1. A method of preventing amplification of a modified nucleic acid contaminant suspected of being present in a sample containing a nucleic acid to be amplified, said method comprising:

(a) combining with said sample a conjugate comprising a specific binding pair (sbp) member bound to a nuclease, wherein said sbp member binds to a modification in said modified nucleic acid contaminant, said modification having been introduced therein in a prior amplification of said nucleic acid, (b) adjusting the temperature and pH of said sample to provide conditions wherein prior to amplification of said nucleic acid to be amplified said sbp member binds to said modified nucleic acid contaminant and said nuclease degrades said modified nucleic acid contaminant but not said nucleic acid, (c) inactivating said nuclease, and (d) amplifying said nucleic acid.

2. The method of claim 1 wherein said amplifying comprises the extension of one or more polynucleotide primers in the presence of deoxynucleoside triphosphates and DNA polymerase wherein at least one of said deoxynucleoside triphosphates is a modified deoxynucleoside triphosphate.

3. The method of claim 1 wherein said amplifying comprises the step of thermally cycling a medium comprised of said sample and at least one oligonucleotide capable of binding to said nucleic acid wherein said oligonucleotide contains a modified nucleotide.

4. A method for conducting amplification of a nucleic acid to produce copies thereof, said method comprising:

(a) providing in combination a sample suspected of containing a nucleic acid and a conjugate comprising a nuclease and a receptor that binds to a modified nucleotide, incorporated into copies of said nucleic acid during amplification of said nucleic acid, and not to said nucleic acid, (b) adjusting the temperature and pH of said combination to provide conditions wherein said receptor binds to said modified nucleotide in said copies and said nuclease degrades said copies without degrading said nucleic acid, wherein said nuclease is deactivated to a level of 50 to 99.9%, (c) inactivating said nuclease, and (d) amplifying said nucleic acid in the presence of reagents including at least one modified nucleoside triphosphate and/or at least one modified oligonucleotide for incorporation of a modified nucleotide into copies of said nucleic acid during said amplifying, one or more of said reagents being present either in said combination prior to step (b) or being added subsequent thereto, said modified nucleoside triphosphate or said modified oligonucleotide being in a protected form if present prior to step (b) and becoming unprotected subsequent to step (b).

5. The method of claim 4 wherein said modified nucleoside triphosphate is selected from the group consisting of alkylated nucleoside triphosphates, halogenated nucleoside triphosphates and nucleoside triphosphates that are covalently bound to a small organic molecule.

6. The method of claim 5 wherein said nucleoside triphosphate is selected from the group consisting of dATP, dTTP, dGTP and dCTP.

7. The method of claim 5 wherein said alkylated nucleoside triphosphate is a methylated deoxyribonucleoside triphosphate.

8. The method of claim 5 wherein said halogenated nucleoside triphosphate is a brominated deoxyribonucleoside triphosphate.

9. The method of claim 5 wherein said small organic molecule is selected from the group consisting of haptens, biotin, and vitamin B12.

10. The method of claim 4 wherein said receptor is an antibody.

11. The method of claim 4 wherein said nuclease is deactivated to a level of 90 to 99%.

12. The method of claim 4 wherein said conditions in step (b) comprise holding said combination at a temperature of 15° to 50° C. for a period of 1 to 60 minutes.

13. The method of claim 4 wherein said conditions in step (c) comprise cycling the temperature of said combination between 80° to 105° C. for a period of 10 to 200 seconds and 40° to 80° C. for a period of 10 to 200 seconds.

14. A method for preparing copies of a nucleic acid, said method comprising:
   (a) combining in a medium (i) a sample suspected of containing a nucleic acid, (ii) reagents for amplifying said nucleic acid comprising deoxyribonucleoside triphosphates selected from the group consisting of dATP, dCTP, dGTP and dTTP, an oligonucleotide, DNA polymerase, and (iii) a conjugate comprising a DNAse and receptor that binds to a modified nucleotide incorporated in a nucleic acid contaminant suspected of being in said medium and not to said nucleic acid,
   (b) adjusting the temperature of said medium to 15° to 50° C. and the pH of said medium to 6 to 10 for a period of 1 to 60 minutes,
   wherein said reagents further comprise at least one modified deoxyribonucleoside triphosphate and/or at least one modified oligonucleotide, said modified deoxyribonucleoside triphosphate and/or said modified oligonucleotide being in a protected form if in said combination prior to step (b) and becoming unprotected in step (c),
   (c) inactivating said DNase, and
   (d) amplifying said nucleic acid to produce copies thereof.

15. The method of claim 14 wherein said modified deoxyribonucleoside triphosphate is selected from the group consisting of alkylated deoxyribonucleoside triphosphates, halogenated deoxyribonucleoside triphosphates and deoxyribonucleoside triphosphates that are covalently bound to a small organic molecule.

16. The method of claim 15 wherein said alkylated deoxyribonucleoside triphosphate is a methylated deoxyribonucleoside triphosphate.

17. The method of claim 15 wherein said halogenated deoxyribonucleoside triphosphate is a brominated deoxyribonucleoside triphosphate.

18. The method of claim 15 wherein said small organic molecule is selected from the group consisting of haptens, biotin, and vitamin B12.

19. The method of claim 14 wherein said receptor is an antibody.

20. The method of claim 14 wherein said pH is adjusted in step (b) to 7 to 9.

21. A method for determining the presence of a polynucleotide analyte, which is a nucleic acid, said method comprising:
   (a) combining in a medium a sample suspected of containing a polynucleotide analyte, reagents for amplifying said polynucleotide analyte to produce copies thereof, said reagents including a polynucleotide polymerase, at least one oligonucleotide primer, nucleoside triphosphates wherein said reagents further comprise at least one modified nucleoside triphosphate and/or at least one modified oligonucleotide primer for incorporation of a modified nucleotide into copies of said nucleic acid during said amplification, one or more of said reagents being in said combination prior to step (b) or being added subsequent thereto, said modified nucleoside triphosphate or said modified oligonucleotide primer being in a protected form if present prior to step (b) and becoming unprotected subsequent to step (b), and a conjugate comprising a nuclease and a receptor that binds to said copies, produced in a prior amplification, and not to said polynucleotide analyte,
   (b) adjusting the temperature of said medium to 15° to 50° C. and the pH of said medium to 6 to 10 for a period of 1 to 60 minutes,
   (c) inactivating said nuclease,
   (d) amplifying said polynucleotide analyte to produce copies thereof by thermal cycling to achieve denaturing of double stranded nucleic acid, hybridization of said oligonucleotide primer to said nucleic acid and extension of said oligonucleotide primer along said nucleic acid and
   (e) detecting said copies of said polynucleotide analyte.

22. The method of claim 21 wherein said polynucleotide analyte is DNA.

23. The method of claim 21 wherein said modified nucleoside triphosphate is selected from the group consisting of alkylated deoxyribonucleoside triphosphates, halogenated deoxyribonucleoside triphosphates and deoxyribonucleoside triphosphates that are covalently bound to a small organic molecule.

24. The method of claim 23 wherein said alkylated deoxyribonucleoside triphosphate is a methylated deoxyribonucleoside triphosphate.

25. The method of claim 23 wherein said halogenated deoxyribonucleoside triphosphate is a brominated deoxyribonucleoside triphosphate.

26. The method of claim 23 wherein said small organic molecule is selected from the group consisting of haptens, biotin, and vitamin B12.

27. The method of claim 21 wherein said receptor is an antibody.

28. The method of claim 21 wherein said pH is adjusted to 7 to 9.

29. The method of claim 21 wherein said copies are detected by means of a labeled probe.

30. The method of claim 21 wherein said oligonucleotide primer is labeled and said copies are detected by means of said label.

31. A method for conducting amplification of a nucleic acid to produce copies thereof, said method comprising:
   (a) providing in combination a sample suspected of containing a nucleic acid, reagents for conducting an amplification of said nucleic acid, said reagents including nucleoside triphosphates, a polynucleotide polymerase, an oligonucleotide primer, a modified nucleoside triphosphate and/or a modified oligonucleotide primer for incorporation of a modified nucleotide into copies of said nucleic acid during said amplification, said modified nucleoside triphosphate and/or said modified oligonucleotide being in protected form, and a conjugate comprising a nuclease and a receptor that binds to said modified nucleotide in said copies, produced in a prior amplification, and not to said nucleic acid, (b) adjusting the temperature of said combination to a temperature of 15° to 50° C. and the pH of said combination to 6 to 10 for a period of 1 to 60 minutes, (c) inactivating said nuclease, (d) releasing said modified nucleoside triphosphate and/or said modified oligonucleotide from said protected form and (e) amplifying said nucleic acid to produce copies thereof by thermal cycling to achieve denaturing of double stranded nucleic acid, hybridization of said oligonucleotide primer to said nucleic acid and extension of said oligonucleotide primer along said nucleic acid.

32. A method for preparing copies of a nucleic acid, said method comprising:

(a) combining in a medium a sample suspected of containing a nucleic acid, deoxyribonucleoside triphosphates selected from the group consisting of dATP, dCTP, dGTP and dTTP, DNA polymerase, at least one oligonucleotide, and a conjugate comprising a DNAse and receptor that binds to a modified nucleotide in a nucleic acid contaminant suspected of being in said medium and not to said nucleic acid, (b) subjecting said medium to a temperature of 15° to 50° C. and a pH of 6 to 10 for a period of 1 to 60 minutes, (c) inactivating said DNase, (d) adding to said combination a modified deoxyribonucleoside triphosphate for incorporation into copies of said nucleic acid and (e) amplifying said nucleic acid by thermal cycling to produce copies thereof.

33. A method for determining the presence of a polynucleotide analyte, said method comprising the steps of:

(a) combining in a medium a sample suspected of containing a polynucleotide analyte, nucleoside triphosphates, a modified nucleoside triphosphate, a polynucleotide polymerase, at least one oligonucleotide primer, wherein optionally said oligonucleotide primer is a modified oligonucleotide primer, said modified nucleoside triphosphate and/or said modified oligonucleotide primer being in protected form, and a conjugate comprising a nuclease and a receptor that binds to a modified nucleotide in a nucleic acid contaminant suspected of being in said medium and not to said nucleic acid, (b) subjecting said medium to a temperature of 15° to 50° C. and a pH of 6 to 10 for a period of 1 to 60 minutes, (c) inactivating said nuclease, (d) amplifying said nucleic acid to produce copies thereof by thermal cycling to achieve denaturing of double stranded nucleic acid, hybridization of said oligonucleotide to said nucleic acid and extension of said oligonucleotide along said nucleic acid and (e) detecting said copies of said polynucleotide analyte.

34. A method of preventing carry-over contamination in amplification of a nucleic acid suspected of being present in a plurality of samples including at least a first sample and a second sample, said method comprising:

(a) during amplification of said first sample incorporating, into copies of said nucleic acid that are produced during said amplification, modified nucleotides that render said copies bindable by a receptor that does not bind to said nucleic acid, (b) prior to subjecting said second sample to amplification, combining said second sample with a receptor bound to a nuclease, under conditions wherein said receptor binds to said copies, which may be present as carry-over contamination, and said nuclease degrades said copies but not said nucleic acid, wherein said nuclease is deactivated to a level of 50 to 99.9%, (c) inactivating said nuclease, and (d) amplifying said nucleic acid in said second sample.

35. A kit comprising in packaged combination:

(a) nucleoside triphosphates wherein at least one of said nucleoside triphosphates is modified, (b) polynucleotide polymerase, (c) at least one oligonucleotide, and (d) a conjugate comprising a nuclease and receptor that binds to an amplified nucleic acid that contains said modified nucleoside triphosphate wherein said receptor does not bind to said nucleic acid.

36. The kit of claim 35 wherein said modified nucleoside triphosphate is selected from the group consisting of alkylated deoxyribonucleoside triphosphates, halogenated deoxyribonucleoside triphosphates and deoxyribonucleoside triphosphates that are covalently bound to a small organic molecule.

37. The kit of claim 36 wherein said alkylated deoxyribonucleoside triphosphate is a methylated deoxyribonucleoside triphosphate.

38. The kit of claim 36 wherein said halogenated deoxyribonucleoside triphosphate is a brominated deoxyribonucleoside triphosphate.

39. The kit of claim 36 wherein said small organic molecule is selected from the group consisting of haptens, biotin and vitamin B12.

40. The kit of claim 35 wherein said receptor is an antibody.

41. The kit of claim 35 wherein said modified nucleoside triphosphate comprises a protective group that prevents said modified nucleoside triphosphate from reacting with said receptor.

42. The kit of claim 35 comprising a labeled probe that binds to said nucleic acid.

43. The kit of claim 35 wherein said oligonucleotide is labeled.

44. The kit of claim 35 wherein said nucleoside triphosphates are selected from the group consisting of dATP, dCTP, dGTP and dTTP, said polynucleotide polymerase is DNA polymerase, said oligonucleotide is a polynucleotide primer, and said nuclease is DNase.

45. A kit for amplifying a nucleic acid comprising in packaged combination a conjugate of a receptor and a nuclease, an oligonucleotide, and nucleoside triphosphates, wherein at least one of said nucleoside triphosphates and said oligonucleotide is modified and wherein said receptor binds to amplified nucleic acid produced from said modified nucleoside triphosphates and said oligonucleotide and not to said nucleic acid.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

ACTGGTAGAG GCGGCGATGG TTGAA                25

( 2 ) INFORMATION FOR SEQ ID NO:2:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

-continued

```
ACTGGTAGAG  GCGGCGATGG  TTGAATAACC  CTGAATTCAG  GGTTAGCCAC  ACTTTGCGGG    60

CACCGTAAAC                                                                70
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
TAGCCCTTGT  CGAACCGCAT  ACCCT                                             25
```

( 2 ) INFORMATION FOR SEQ ID NO:4:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

```
TAGCCCTTGT  CGAAGCGCAT  ACCCTGTGTG  TCCATATGGA  CACACCATCG  TTGGTGATCG    60

TGGGGGCACC                                                                70
```